United States Patent
Xu et al.

(10) Patent No.: US 10,717,986 B1
(45) Date of Patent: Jul. 21, 2020

(54) RESISTANCE ALLELES IN SOYBEAN

(71) Applicant: Syngenta Participations AG, Basel (CH)

(72) Inventors: Zhanyou Xu, Slater, IA (US); Ju-Kyung Yu, Slater, IA (US); Becky Welsh Breitinger, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/043,251

(22) Filed: Jul. 24, 2018

Related U.S. Application Data

(62) Division of application No. 14/945,906, filed on Nov. 19, 2015, now Pat. No. 10,053,705.

(60) Provisional application No. 62/082,382, filed on Nov. 20, 2014.

(51) Int. Cl.
*A01H 5/10* (2018.01)
*C12N 15/82* (2006.01)
*C12Q 1/6895* (2018.01)

(52) U.S. Cl.
CPC .......... *C12N 15/8282* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,689,035 | A | 11/1997 | Webb |
| 5,948,953 | A | 9/1999 | Webb |
| 7,919,675 | B2 | 4/2011 | Godwin et al. |
| 8,193,411 | B2 | 6/2012 | Godwin et al. |
| 2010/0132067 | A1 | 5/2010 | Godwin et al. |
| 2010/0240061 | A1 | 9/2010 | Butruille et al. |

FOREIGN PATENT DOCUMENTS

WO  2014/150226  3/2014

OTHER PUBLICATIONS

James Brewer Blessitt, 2013, Characterization, inheritance, and marker identification of potential novel genes conditioning resistance to multiple races of Cercospora sojina K. Hara of soybean (*Glycine max* L.), PhD thesis, Mississippi State University, pp. 1-115.*
Genetic map of soybean chromosome 16, obtained from the SoyBase database, www.soybase.org, published Sep. 30, 2017.*
Bacman,M.S. and Nickell,C.D.,"Investigating the genetic model for brown stem rot resistance in soybean," The Journal of Heredity, 2000:91(4); p. 316-321.
Bachman et al., "Molecular markers linked to brown stem rot resistance genes, Rbs1 and Rbs2, in soybean," Crop Sci. 2001, 41:527-535.
Demirbas et al., "Simple sequence repeat markers linked to the soybean Rps genes for phytophthora resistance," Crop Sci., 2001, 41:1220-1227.
Filho et al., "RAPD and SCAR markers linked to resistance to frogeye leaf spot in soybean," Genetics and Molecular Biology, 2002, 25(3):317-321.
Guzman et al., "QTL associated with yield in three backcross-derived populations of soybean," Crop Sci. 2007, 47:111-122.
Ha and Boerma, "High-throughput SNP genotyping by melting curve analysis for resistance to Souther root-knot nematode and frogeye leaf spot in soybean," J. Crop Sci. Biotech Jun. 2008, 11(2):91-100.
Hanson et al., "Identification of two dominant genes conditioning brown stem rot resistance in soybean," Crop Sci. 1988, 28:41-43.
Hughes, et al., "Resistance to brown stem rot in soybean germ plasm with resistance to the soybean cyst nematode," Plant Disease, 2004, 88(7): 761-768.
Kang, et al., "Genome-wide mapping of NBS-LRR genes and their association with disease resistance in soybean," BMC Plant Biology 2012, 12:139; p. 13.
Klos et al., "Molecular markers useful for detecting resistance to brown stem rot in soybean," Crop Sci. 2000, 40:1445-1452.
Lewers et al., "Detection of linked QTL for soybean brown stem rot resistance in 'BSR 101' as expressed in a growth chamber environment," Molecular Breeding 1999, 5:33-42.
Missaoui et al., "Single nucleotide polymorphism detection of the Rcs3 gene for resistance to frogeye leaf spot in soybean," Crop Science, 2007, vol. 47, 1681-1690.
Patzoldt et al., "Localization of a quantitative trait locus providing brown stem rot resistance in the soybean cultivar bell," Crop Science, 2005, 45:1241-1248.
Rouf Mian et al., "Molecular mapping of the Rcs3 gene for resistance to frogeye leaf spot in soybean," Crop Sci. 1999, 39:1687-1691.
Yang et al., Molecular mapping of a new gene for resistance to frogeye leaf spot of soya bean in 'Peking', Plant Breeding, 2001, 120:73-78.
Soybase Soybean Genetic Map, chromosome 16, available at https://www.soybase.org/, accessed Sep. 30, 2017.
SNP Report for BARC-042895-08450, SoyBase database, available at https://www.soybase.org, accessed Sep. 30, 2017.

* cited by examiner

*Primary Examiner* — Bratislav Stankovic
(74) *Attorney, Agent, or Firm* — R. Kody Jones

(57) ABSTRACT

The present invention relates to methods and compositions for identifying, selecting and/or producing a soybean plant or germplasm having brown stem rot (BSR) and/or frogeye leaf spot (FLS) resistance. A soybean plant, part thereof and/or germplasm, including any progeny and/or seeds derived from a soybean plant or germplasm identified, selected and/or produced by any of the methods of the present invention is also provided.

5 Claims, No Drawings
Specification includes a Sequence Listing.

RESISTANCE ALLELES IN SOYBEAN

RELATED APPLICATION INFORMATION

This Application is a divisional of U.S. patent Ser. No. 14/945,906 filed Nov. 19, 2015 that claims the benefit of U.S. Provisional Application No. 62/082,382, filed 20 Nov. 2014, the contents of which are incorporated herein by reference herein.

STATEMENT REGARDING ELECTRONIC FILING OF A SEQUENCE LISTING

A Sequence Listing in ASCII text format, submitted under 37 C.F.R. § 1.821, entitled 80648_ST25.txt, 15.8 kilobytes in size, generated on Nov. 11, 2015 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and/or producing soybean plants having brown stem rot (BSR) and/or frogeye leaf spot (FLS) resistance.

BACKGROUND

Brown stem rot (BSR) is one of the most frequently occurring and devastating diseases of soybean in soybean planting regions worldwide. BSR is caused by the soil-borne fungus *Phialophora gregata*. BSR-infected plants can exhibit reduced photosynthate availability during seed filling that results in yield loss as high as 66%.

Frog eye leaf spot (FLS) disease is caused by a fungus that primarily attacks soybean foliage. However, the fungus can also attack seeds, pods, and stems. Frog eye spots reduce photosynthetic area on infected leaves and significantly reduce soybean productivity when numerous. Ethylene produced in the leaf spots promotes premature defoliation, further reducing productivity. Development of the disease is favored by warm, humid conditions. The disease has historically been most important in the warm, humid Southeastern states of the USA but its distribution has increasingly widened to include the southern Midwest.

The most common symptoms of FLS disease encountered on soybean plants are circular to angular spots on leaves that resemble the eyes of frogs, giving the disease its name Lesions begin as dark, water-soaked spots, with or without lighter centers and develop into brown spots surrounded by narrow, dark reddish brown margins <1-5 mm in diameter. Older spots are light to dark brown, translucent, and have white centers containing minute dark stromata. Several spots may coalesce to form larger, irregular spots. When spots cover about 30% of the leaf area, a blighting phase often occurs, and leaves wither and fall prematurely.

The causal organism of FLS disease is *Cercospora sojina* Hara. Conidiophores (4-6×52-120 mm) arise in fascicles of two to 25 from a thin stroma, light to dark brown in color with one to several septa, covered with prominent bands (geniculations) and scars left by detached conidia. Conidia or sympodulospores are indeterminately borne successively on new growing tips of the conidiophores, hyaline or dark colored, filiform (scolecospores), multiseptate. Multiple pathotypes exist.

Spots normally appear 8-12 days following inoculation with conidia, however, under continuous moist, warm conditions, spots may appear as early as 48 hrs post-inoculation. Conidia carried short distances by air currents and splashing rain cause secondary infections under favorable conditions throughout the season.

Deployment of cultivars possessing the Rcs3 gene that gives resistance to known pathotypes is the primary means to manage the disease. Registered fungicides applied at growth stages R2-R5 can effectively control the disease on susceptible soybean cultivars. Fungicides applied to the seed will control seed-borne infection.

Thus, the present invention overcomes shortcomings in the art by providing markers associated with resistance to brown stem rot (BSR) and markers associated with resistance to frogeye leaf spot (FLS), thereby allowing the characterization of soybean cultivars for such resistance by molecular analysis.

SUMMARY OF THE INVENTION

Compositions and methods for identifying, selecting and/or producing soybean plants with brown stem rot (BSR) and/or frogeye leaf spot (FLS) resistance are provided. As described herein, a marker associated with BSR and/or FLS resistance may comprise, consist essentially of or consist of a single allele or a combination of alleles at one or more genetic loci.

In some embodiments, the present invention provides a method of identifying and/or selecting a brown stem rot (BSR) resistant soybean plant or part thereof, comprising: detecting, in said soybean plant or part thereof, at least one allele of a marker locus that is associated with BSR resistance in a soybean plant, wherein said one or more marker locus is located within a chromosome interval selected from the group consisting of: (a) a chromosome interval on chromosome 16 defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c) a chromosome interval on chromosome 16 defined by and including base pair (bp) position 31,292,707 (SY0090) to base pair (bp) position 33,324,409 (SY3126), thereby identifying and/or selecting a BSR resistant soybean plant or part thereof.

In some embodiments, the present invention provides a method of identifying and/or selecting a brown stem rot (BSR) resistant soybean plant or part thereof, comprising: detecting, in said soybean plant or part thereof, the presence of a marker associated with BSR resistance in a soybean plant, wherein said marker is located within a chromosome interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, thereby identifying and/or selecting a BSR resistant soybean plant or part thereof.

In some embodiments, the present invention provides a method of identifying and/or selecting a brown stem rot (BSR) resistant soybean plant or part thereof, comprising: detecting, in said soybean plant or part thereof, the presence of a marker associated with BSR resistance, wherein said marker is selected from the group consisting of: (a) a G allele at SY0090; (b) a T allele at SY0871; (c) a G allele at SY3126; and (d) any combination of (a) through (c) above, thereby identifying and/or selecting a BSR resistant soybean plant or part thereof.

In some embodiments, the present invention provides a method of identifying and/or selecting a brown stem rot (BSR) resistant soybean plant or part thereof, comprising: detecting, in said soybean plant or part thereof, the presence of a combination of markers associated with BSR resistance in a soybean plant, wherein said combination of markers is selected from the group consisting of: (a) a T allele at SY0871 and a G allele at SY3126 (b) a T allele at SY0871 and a G allele at SY0090; (c) a G allele at SY3126 and a G allele at SY0090; and (d) a T allele at SY0871 and a G allele at SY3126 and a G allele at SY0090, thereby identifying and/or selecting a BSR resistant soybean plant or part thereof.

In some embodiments, the present invention provides a method of identifying and/or selecting a brown stem rot (BSR) resistant soybean plant or part thereof, comprising: detecting, in said soybean plant or part thereof, at least one allele of a marker locus that is associated with BSR resistance in a soybean plant, wherein said one or more marker locus is located within a chromosome interval on chromosome 16 defined by and including markers Sat_350 (physical position 30036787) and Satt431 (physical position 35718476), thereby identifying and/or selecting a BSR resistant soybean plant or part thereof.

In some embodiments, the present invention provides a method of producing a brown stem rot (BSR) resistant soybean plant, comprising: detecting, in said soybean plant or part thereof, at least one allele of a marker locus that is associated with BSR resistance in a soybean plant, wherein said one or more marker locus is located within a chromosome interval selected from the group consisting of: (a) a chromosome interval on chromosome 16 defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c), a chromosome interval on chromosome 16 defined by and including base pair (bp) position 31,292,707 (SY0090) to base pair (bp) position 33,324,409 (SY3126), thereby producing a BSR resistant soybean plant or part thereof.

In some embodiments, the present invention provides a method of producing a brown stem rot (BSR) resistant soybean plant, comprising: detecting, in a soybean germplasm, the presence of a marker associated with BSR resistance in a soybean plant, wherein said marker is located within a chromosome interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, and producing a soybean plant from said soybean germplasm, thereby producing a brown stem rot (BSR) resistant soybean plant.

In some embodiments, the present invention provides a method of producing a brown stem rot (BSR) resistant soybean plant, comprising: detecting, in a soybean germplasm, the presence of a combination of markers associated with BSR resistance in a soybean plant, wherein said combination of markers is selected from the group consisting of: (a) a G allele at SY0090 and a T allele at SY0871; (b) a T allele at SY0871 and a G allele at SY3126; (c) a G allele at SY0090 and a G allele at SY3126; and (d) a G allele at SY0090 and a T allele at SY0871 and a G allele at SY3126, and producing a soybean plant from said soybean germplasm, thereby producing a BSR resistant soybean plant.

In some embodiments, the present invention provides a method of producing a brown stem rot (BSR) resistant soybean plant, comprising: detecting, in a soybean germplasm, the presence of a marker associated with BSR resistance in a soybean plant, wherein said marker is selected from the group consisting of: (a) a G allele at SY0090; (b) a T allele at SY0871; (c) a G allele at SY3126; and (d) any combination of (a) through (c) above, and producing a soybean plant from said soybean germplasm, thereby producing a BSR resistant soybean plant. It is envisioned that one skilled in the art could produce a soy plant resistant to BSR or FLS either through conventional plant breeding, through transgenic expression (e.g. locating genes within the intervals described and/or in or near the markers displayed herein), also one may employ the technologies of gene editing such as TALEN or CRISPR to create resistant lines by making the allele/sequence changes suggested herein.

In some embodiments, the present invention provides a method of producing a brown stem rot (BSR) resistant soybean plant or part thereof, comprising: detecting, in said soybean plant or part thereof, at least one allele of a marker locus that is associated with BSR resistance in a soybean plant, wherein said one or more marker locus is located within a chromosome interval on chromosome 16 defined by and including markers Sat_350 (physical position 30036787) and Satt431 (physical position 35718476), thereby producing a BSR resistant soybean plant or part thereof.

In some embodiments, the present invention provides a method of selecting a brown stem rot (BSR) resistant soybean plant or germplasm, comprising: crossing a first soybean plant or germplasm with a second soybean plant or germplasm, wherein said first soybean plant or germplasm comprises within its genome a marker associated with BSR resistance in a soybean plant, wherein said marker is located within a chromosome interval selected from the group consisting of: (a) a chromosome interval on chromosome 16 defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c) a chromosome interval on chromosome 16 defined by and including base pair (bp) position 31,292,707 (SY0090) to base pair (bp) position 33,324,409 (SY3126), and selecting a progeny soybean plant or germplasm that comprises said marker within its genome, thereby selecting a BSR resistant soybean plant or germplasm.

In some embodiments, the present invention provides a method of selecting a brown stem rot (BSR) resistant soybean plant or germplasm, comprising: crossing a first soybean plant or germplasm with a second soybean plant or germplasm, wherein said first soybean plant or germplasm comprises within its genome a marker associated with BSR resistance in a soybean plant, wherein said marker is located within a chromosome interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, and selecting a progeny soybean plant or germplasm that comprises said marker within its genome, thereby selecting a BSR resistant soybean plant or germplasm.

In some embodiments, the present invention provides a method of selecting a brown stem rot (BSR) resistant soybean plant or germplasm, comprising: crossing a first soybean plant or germplasm with a second soybean plant or germplasm, wherein said first soybean plant or germplasm comprises within its genome a combination of genetic markers associated with BSR resistance in a soybean plant, the combination of genetic markers selected from the group consisting of: (a) a T allele at SY0871 and a G allele at SY3126 (b) a T allele at SY0871 and a G allele at SY0090; (c) a G allele at SY3126 and a G allele at SY0090; and (d) a T allele at SY0871 and a G allele at SY3126 and a G allele at SY0090, and selecting a progeny soybean plant or germplasm that comprises said combination of markers within its genome, thereby selecting a BSR resistant soybean plant or germplasm.

In some embodiments, the present invention provides a method of selecting a brown stem rot (BSR) resistant soybean plant or germplasm, comprising: crossing a first soybean plant or germplasm with a second soybean plant or germplasm, wherein said first soybean plant or germplasm comprises within its genome a marker associated with BSR resistance in a soybean plant, wherein said marker is selected from the group consisting of: (a) a G allele at SY0090; (b) a T allele at SY0871; (c) a G allele at SY3126; and (d) any combination of (a) through (c) above, and selecting a progeny soybean plant or germplasm that comprises said marker within its genome, thereby selecting a BSR resistant soybean plant or germplasm.

In some embodiments, the present invention provides a method of selecting brown stem rot (BSR) resistant soybean plant or germplasm, comprising: crossing a first soybean plant or germplasm with a second soybean plant or germplasm, wherein said first soybean plant or germplasm comprises within its genome a marker associated with BSR resistance in a soybean plant, wherein said marker is located within a chromosome interval on chromosome 16 defined by and including markers Sat_350 (physical position 30036787) and Satt431 (physical position 35718476); and selecting a progeny soybean plant or germplasm that comprises said marker within its genome, thereby selecting a BSR resistant soybean plant or germplasm.

In some embodiments, the present invention provides a method of identifying and/or selecting a frogeye leaf spot (FLS) resistant soybean plant or part thereof, comprising: detecting, in said soybean plant or part thereof, at least one allele of a marker locus that is associated with FLS resistance in a soybean plant, wherein said one or more marker locus is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), thereby identifying and/or selecting a FLS resistant soybean plant or part thereof.

In some embodiments, the present invention provides a method of identifying and/or selecting a frogeye leaf spot (FLS) resistant soybean plant or part thereof, comprising: detecting, in said soybean plant or part thereof, the presence of a marker associated with FLS resistance in a soybean plant, wherein said marker is located within a chromosome interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, thereby identifying and/or selecting a FLS resistant soybean plant or part thereof.

In some embodiments, the present invention provides a method of identifying and/or selecting a frogeye leaf spot (FLS) resistant soybean plant or part thereof, comprising: detecting, in said soybean plant or part thereof, the presence of a marker associated with FLS resistance, wherein said marker is selected from the group consisting of: (a) an A allele at SY3122; (b) a D allele at SY0141; (c) an A allele at SY3124; and (d) any combination of (a) through (c) above, thereby identifying and/or selecting a FLS resistant soybean plant or part thereof.

In some embodiments, the present invention provides a method of identifying and/or selecting a frogeye leaf spot (FLS) resistant soybean plant or part thereof, comprising: detecting, in said soybean plant or part thereof, the presence of a combination of markers associated with FLS resistance in a soybean plant, wherein said combination of markers is selected from the group consisting of: (a) an A allele at SY3122 and a D allele at SY0141 (b) an A allele at SY3122 and an A allele at SY3124; (c) a D allele at SY0141 and an A allele at SY3124; and (d) an A allele at SY3122 and a D allele at SY0141 and an A allele at SY3124, thereby identifying and/or selecting a FLS resistant soybean plant or part thereof.

In some embodiments, the present invention provides a method of identifying and/or selecting a frogeye leaf spot (FLS) resistant soybean plant or part thereof, comprising: detecting, in said soybean plant or part thereof, at least one allele of a marker locus that is associated with FLS resistance in a soybean plant, wherein said one or more marker locus is located within a chromosome interval on chromosome 16 defined by and including markers Sat244 and Satt547, thereby producing a FLS resistant soybean plant or part thereof.

In some embodiments, the present invention provides a method of producing a frogeye leaf spot (FLS) resistant soybean plant, comprising: detecting, in said soybean plant or part thereof, at least one allele of a marker locus that is associated with FLS resistance in a soybean plant, wherein said one or more marker locus is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), thereby producing a FLS resistant soybean plant or part thereof.

In some embodiments, the present invention provides a method of producing a frogeye leaf spot (FLS) resistant soybean plant, comprising: detecting, in a soybean germplasm, the presence of a marker associated with FLS resistance in a soybean plant, wherein said marker is located within a chromosome interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, and producing a soybean plant from said soybean germplasm, thereby producing a frogeye leaf spot (FLS) resistant soybean plant.

In some embodiments, the present invention provides a method of producing a frogeye leaf spot (FLS) resistant soybean plant, comprising: detecting, in a soybean germplasm, the presence of a combination of markers associated with FLS resistance in a soybean plant, wherein said combination of markers is selected from the group consisting of: (a) an A allele at SY3122 and a D allele at SY0141; (b) a D allele at SY0141 and an A allele at SY3124; (c) an A allele at SY3122 and an A allele at SY3124; and (d) an A allele at SY3122 and a D allele at SY0141 and an A allele at SY3124, and producing a soybean plant from said soybean germplasm, thereby producing a FLS resistant soybean plant.

In some embodiments, the present invention provides a method of producing a frogeye leaf spot (FLS) resistant soybean plant, comprising: detecting, in a soybean germplasm, the presence of a marker associated with FLS resistance in a soybean plant, wherein said marker is selected from the group consisting of: (a) an A allele at SY3122; (b) a D allele at SY0141; (c) an A allele at SY3124; and (d) any combination of (a) through (c) above, and producing a soybean plant from said soybean germplasm, thereby producing a FLS resistant soybean plant.

In some embodiments, the present invention provides a method of producing a frogeye leaf spot (FLS) resistant soybean plant or part thereof, comprising: detecting, in said soybean plant or part thereof, at least one allele of a marker locus that is associated with FLS resistance in a soybean plant, wherein said one or more marker locus is located within a chromosome interval on chromosome 16 defined by and including markers Sat244 and Satt547, thereby producing a FLS resistant soybean plant or part thereof.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), and selecting a progeny soybean plant or germplasm that comprises said marker within its genome, thereby selecting a FLS resistant soybean plant or germplasm.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is located within a chromosome interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, and selecting a progeny soybean plant or germplasm that comprises said marker within its genome, thereby selecting a FLS resistant soybean plant or germplasm.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a combination of genetic markers associated with FLS resistance in a soybean plant, the combination of genetic markers selected from the group consisting of: (a) an A allele at SY3122 and a D allele at SY0141; (b) a D allele at SY0141 and an A allele at SY3124; (c) an A allele at SY3122 and an A allele at SY3124; and (c) an A allele at SY3122 and a D allele at SY0141 and an A allele at SY3124, and selecting a progeny soybean plant or germplasm that comprises said marker within its genome, thereby selecting a FLS resistant soybean plant or germplasm.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is selected from the group consisting of: (a) an A allele at SY3122; (b) a D allele at SY0141; (c) an A allele at SY3124; and (d) any combination of (a) through (c) above, and selecting a progeny soybean plant or germplasm that comprises said marker within its genome, thereby selecting a FLS resistant soybean plant or germplasm.

It is contemplated that the genotypes described herein can be used in combination with commercial fungicides to control BSR and FLS symptoms or confer resistance.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is located within a chromosome interval on chromosome 16 defined by and including markers Sat244 and Satt547; and selecting a progeny soybean plant or germplasm that comprises said marker within its genome, thereby selecting a FLS resistant soybean plant or germplasm.

These and other aspects of the invention are set forth in more detail in the description of the invention below.

DETAILED DESCRIPTION

The present invention provides compositions and methods for identifying, selecting and/or producing soybean plants having brown stem rot (BSR) resistance and/or frogeye leaf spot (FLS) resistance, as well as soybean plants, parts thereof, including but not limited to seeds, and soybean germplasm, that are identified, selected and/or produced by methods of this invention. The present invention further provides an assay for the detection of BSR and/or FLS resistance in a soybean plant, plant part and/or soybean germplasm. In addition, the present invention provides soybean plants, plant parts, and/or germplasm having within their genome one or more SNP or QTL markers associated with resistance to brown stem rot (BSR) disease and/or frogeye leaf spot (FLS) disease.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising." As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with brown stem rot resistance in a soybean plant relative to a control soybean plant not having the target allele or alleles. Thus, for example, a soybean plant comprising one or more of the markers associated with BSR and/or FLS resistance as described herein (e.g., desired alleles) can have BSR and/or FLS resistance or increased BSR and/or FLS resistance as compared to a soybean plant that does not comprise said one or more markers associated with BSR and/or FLS resistance (e.g., desired alleles).

A marker is "associated with" a trait when said trait is linked to the marker and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with a BSR and/or FLS resistance allele" refers to a marker whose presence or absence can be used to predict whether a plant will display BSR and/or FLS resistance.

As used herein, the terms "backcross" and "backcrossing" refer to the process whereby a progeny plant is crossed back to one of its parents one or more times (e.g., 1, 2, 3, 4, 5, 6, 7, 8, 9, 10, or more.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some embodiments, the number of backcrosses can be about 1 to about 10 (e.g., 1, 2, 3, 4, 5, 6, 7, 8, 9, 10). In some embodiments, the number of backcrosses is about 7.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make up for all the genes in its genome. Genotypes can be indirectly characterized, e.g., using markers and/or directly characterized by, e.g., nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.). In some embodiments, germplasm includes but is not limited to tissue culture.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, SY0090 is interchangeable with SY0090A; SY0871 is interchangeable with SY0871AQ; and SY0141 is interchangeable with SY0141AQ and SY0141A. Also as used herein, "chromosome J" is interchangeable with "chromosome 16."

As used herein "D" means deletion and "I" means insertion. For example, the allele for SY0141 is described herein as either D or I. Thus, "D" indicates that the nucleotide sequence TGTA is not present at SY0141 (bp position 33,311,672) and "I" indicates that the nucleotide sequence TGTA is present at SY0141 (bp position 33,311,672).

As used herein, the term "hybrid" in the context of plant breeding refers to a plant that is the offspring of genetically dissimilar parents produced by crossing plants of different lines or breeds or species, including but not limited to a cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, 5, 6, 7, 8, 9, 10 or more times) to a line having a desired genetic background, selecting for the desired allele, with the result being that the desired allele becomes fixed in the desired genetic background. For example, a marker associated with BSR resistance may be introgressed from a donor into a recurrent parent that is BSR susceptible. The resulting offspring could then be backcrossed one or more times and selected until the progeny comprises the genetic marker(s) associated with BSR resistance in the recurrent parent background.

As used herein, the term "linkage" refers to the degree with which one marker locus is associated with another marker locus or some other locus (for example, a BSR or FLS resistance locus). The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., BSR or FLS resistance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., Nature Reviews Genetics 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, Trends in Genetics 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234: 177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (soybase.org). In some embodiments, a genetic marker of this invention is a SNP allele, a SNP allele located in a chromosome interval and/or a haplotype (combination of SNP alleles), each of which is associated with BSR and/or FLS resistance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein.

Accordingly, in some embodiments of this invention, a marker is detected by amplifying a *Glycine* sp. nucleic acid with two oligonucleotide primers by, for example, an amplification reaction such as the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "probe" refers to a single-stranded oligonucleotide sequence that will form a hydrogen-bonded duplex with a complementary sequence in a target nucleic acid sequence analyte or its cDNA derivative. Thus, a "marker probe" and "probe" refers to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of a probe of this invention include SEQ ID NO:4 (SY3126; C allele), SEQ ID NO:5 (SY3126; G allele), SEQ ID NO:9 (SY0871; T allele), SEQ ID NO:10 (SY0871; A allele), SEQ ID NO:14 (SY0090; A allele), SEQ ID NO:15 (SY0090; G allele), SEQ ID NO:19 (SY0141; I allele), SEQ ID NO:20 (SY0141; D allele), SEQ ID NO:24 (SY3122; A allele), SEQ ID NO:25 (SY3122; T allele), SEQ ID NO:29 (SY3124; A allele), and/or SEQ ID NO:30 (SY3124; C allele).

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein can also be referred to as hybridization markers when located on an indel region. This is because the insertion region is, by definition, a polymorphism vis-â-vis a plant without the insertion. Thus, the marker need only indicate whether the indel region is present or absent. Any suitable marker detection technology may be used to identify such a hybridization marker, e.g., technology for SNP detection.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

Non-limiting examples of primers of the invention include SEQ ID NO:2 (SY3126F1), SEQ ID NO:3 (SY3126R1), SEQ ID NO:7 (SY0871AF1), SEQ ID NO:8 (SY0871AR1), SEQ ID NO:12 (SY0090F1), SEQ ID NO:13 (SY0090R1) SEQ ID NO:17 (SY0141AF1), SEQ ID NO:18 (SY0141AR1), SEQ ID NO:22 (SY3122F1), SEQ ID NO:23 (SY3122R1), SEQ ID NO:27 (SY3124F1) and/or SEQ ID NO:28 (SY3124R1).

The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); Computer *Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least abut 50%, 60%, 70%, 75%, 80%, 85%, 90% or 95% sequence identity. In some embodiments, two nucleotide sequences can have at least about 75%, 80%, 85%, 90%, 95%, or 100% sequence identity, and any range or value therein. In representative embodiments, two nucleotide sequences can have at least about 95%, 96%, 97%, 98%, 99% or 100% sequence identity, and any range or value therein.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs, which are publicly available from National Center Biotechnology Information (NCBI) at the National Library of Medicine, National Institute of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence, BLAST®X can be used to determine sequence identity; and for polynucleotide sequence, BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant part or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine max*.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "reference sequence" refers to a defined nucleotide sequence used as a basis for nucleotide sequence comparison (e.g., Chromosome 10 or Chromosome 13 of *Glycine max* cultivar Williams 82). The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

Genetic loci correlating with particular phenotypes, such as root nematode resistance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with brown stem rot (BSR) resistance and/or frogeye leaf spot (FLS) resistance in soybean. Detection of these markers and/or other linked markers can be used to identify, select and/or produce soybean plants having BSR and/or FLS resistance and/or to eliminate soybean plants from breeding programs or from planting that do not have BSR and/or FLS resistance.

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) Genomics 20:176-183.

Table 1 and Table 2, respectively, provide the names of three BSR resistance and three FSL resistance associated markers (SNPs) of this invention, the physical genetic locations of each marker on the respective soybean chromosome or linkage group, and the target allele that is associated with resistance to BSR or FLS, respectively.

Markers of the present invention are described herein with respect to the positions of marker loci in the 8X public build of the Williams 82.a1 (Wm82.a1) soybean genome at the SoyBase internet resource (soybase.org/SequenceIntro.php) or USDA at (bfgLanri.barc.usda.gov/cgi-bin/soybean/Linkage.p1).

TABLE 1

The respective soybean chromosome or linkage group of physical and genetic positions including the sequence identifiers for the DNA fragments comprising the SNPs and two probe sequences with tagged SNP allele for each assay for genetic markers for brown stem rot (BSR) resistance.

| Index | Assay name | Public SNP name/Locus name | Chromosome | Physical position in Williams82 genome | Linkage Group | LG position (cM) | SEQ ID NO for DNA fragment comprising SNP | SEQ ID NO for probe 1 sequence | Probe 1 detected nucleotide | SEQ ID NO for probe 2 sequence | Probe 2 detected nucleotide |
|---|---|---|---|---|---|---|---|---|---|---|---|
| 1 | SY3126 | dbSNP in Glyma 16g29520 | 16 | 33324409 | J | 156 | 1 | 4 | C | 5 | G |
| 2 | SY0871 | BARC-028369-05854 | 16 | 31869001 | J | 149.3 | 6 | 9 | T | 10 | A |

TABLE 1-continued

The respective soybean chromosome or linkage group of physical and genetic positions including the sequence identifiers for the DNA fragments comprising the SNPs and two probe sequences with tagged SNP allele for each assay for genetic markers for brown stem rot (BSR) resistance.

| Index | Assay name | Public SNP name/Locus name | Chromosome | Physical position in Williams82 genome | Linkage Group | LG position (cM) | SEQ ID NO for DNA fragment comprising SNP | SEQ ID NO for probe 1 sequence | Probe 1 detected nucleotide | SEQ ID NO for probe 2 sequence | Probe 2 detected nucleotide |
|---|---|---|---|---|---|---|---|---|---|---|---|
| 3 | SY0090 | BARC-042895-08450 | 16 | 31292707 | J | 144.6 | 11 | 14 | A | 15 | G |

TABLE 2

The respective soybean chromosome or linkage group of physical and genetic positions including sequence indentifiers for the DNA fragments comprising the SNPs and two probe sequences with tagged SNP allele for each assay for genetic markers for frogeye lead spot (FLS) resistance.

| Index | Assay name | Public SNP name/Locus name | Chromosome | Physical position in Williams82 genome | Linkage Group | LG position (cM) | SEQ ID NO for DNA fragment comprising SNP | SEQ ID NO for probe 1 sequence | Probe 1 detected nucleotide | SEQ ID NO for probe 2 sequence | Probe 2 detected nucleotide |
|---|---|---|---|---|---|---|---|---|---|---|---|
| 1 | SY0141 | Designed from BAC seq AZ044573, linked to Satt244 associated with FLS resistance Rcs3 | 16 | 33311672 | J | 156 | 16 | 19 | I | 20 | D |
| 2 | SY3122 | Solexa variant (Syngenta internal; no equivalent BARC SNP known) | 16 | 33267437 | J | 156 | 21 | 24 | A | 25 | T |
| 3 | SY3124 | dbSNP in Glyma16g29520 | 16 | 33322599 | J | 156 | 26 | 29 | A | 30 | C |

Thus, in some embodiments of this invention, the marker alleles associated with brown stem rot (BSR) resistance are as set forth in Table 1. In some embodiments of this invention, the marker allele(s) associated with brown stem rot resistance as set forth in Table 1 can be located in (a) a chromosome interval on chromosome 16 (as used herein, "chromosome 16" can also refer to "chromosome J") defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c) a chromosome interval on chromosome 16 defined by and including base pair (bp) position 31,292,707 (SY0090) to base pair (bp) position 33,324,409 (SY3126). In some embodiments, bp position 31,292,707 (SY0090) comprises a G allele, bp position 31,869,001 (SY0871) comprises a T allele, and/or bp position 33,324,409 (SY3126) comprises a G allele. In further embodiments, the G allele at bp position 31,292,707 (SY0090) can be homozygous, the T allele at bp position 31,869,001 (SY0871) can be homozygous, and/or the G allele at bp position 33,324,409 (SY3126) can be homozygous. As would be understood by one of skill in the art, additional chromosomal intervals can be defined by the SNP markers provided herein in Table 1.

In some embodiments, a marker allele(s) associated with BSR resistance can be located in a chromosome interval defined by and including (a) a chromosome interval on chromosome 16 (chromosome 16) defined by and including markers Sat_350 (physical position 30036787) and Satt431 (physical position 35718476).

In some embodiments, a genetic marker of this invention as set forth in Table 1 is associated with BSR resistance, wherein the genetic marker includes but is not limited to: (a) a G allele at SY0090; (b) a T allele at SY0871; (c) a G allele at SY3126; (d) a GG allele at SY0090; (e) a TT allele at SY0871; (f) a GG allele at SY3126, and any combination of (a) through (f) above. Nonlimiting examples of combinations of this invention include (a) a T allele at SY0871 and a G allele at SY3126; (b) a T allele at SY0871 and a G allele at SY0090; (c) a G allele at SY3126 and a G allele at SY0090; and (d) a T allele at SY0871 and a G allele at SY3126 and a G allele at SY0090.

Accordingly, this invention further provides methods of identifying, selecting, and/or producing a brown stem rot (BSR) resistant soybean plant or part thereof, comprising: detecting, in said soybean plant or part thereof, the presence of a combination of genetic markers associated with BSR resistance in a soybean plant, as described herein. In further embodiments, the marker can comprise, consist essentially of or consist of any marker linked to the aforementioned markers. That is, any genetic marker that is in linkage disequilibrium with any of the aforementioned markers (SNPs, chromosome intervals and/or combinations of markers (haplotypes)) may also be used to identify, select and/or produce a soybean plant having BSR resistance. Linked markers may be determined, for example, by using resources available on the SoyBase website (soybase.org).

The present invention further provides that the detecting of a molecular marker can comprise the use of a nucleic acid probe having a nucleotide base sequence that is substantially complementary to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of an SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 90%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencers. Such methods of detecting an amplified DNA fragment are not described here in detail as they are well known to those of ordinary skill in the art.

As shown in Table 1, the SNP markers of this invention are associated with BSR resistance. In some embodiments, as described herein, one marker or a combination of markers can be used to detect the presence of a BSR resistant plant. In some embodiments, a marker can be located within a chromosomal interval (QTL) or be present in the genome of the plant (e.g., as a haplotype as defined herein).

Thus, methods for identifying and/or selecting a soybean plant or germplasm comprising BSR resistance comprise detecting the presence of a genetic marker (e.g., SNP, SNP located in chromosomal interval (QTL) and/or combination of SNPs) associated with BSR resistance in a soybean plant or part thereof. The genetic marker can be detected in any sample taken from the soybean plant or from a soybean germplasm, including, but not limited to, the whole plant or germplasm or any part thereof (e.g., a seed, a leaf, a tissue culture, a cell, etc.).

Accordingly, in some aspects of the present invention, a method of identifying and/or selecting a BSR resistant soybean plant or part thereof is provided, the method comprising: detecting, in said soybean plant or part thereof, the presence of a marker associated with BSR resistance in a soybean plant, wherein said marker is located within a chromosome interval comprising, consisting essentially of, or consisting of (a) a chromosome interval on chromosome 16 defined by and including base pair (bp) position 31292707 (SY0090) to base pair (bp) position 31869001 (SY0871); (b) a chromosome interval on chromosome 16 defined by and including base pair (bp) position 31869001 (SY0871) to base pair (bp) position 33324409 (SY3126); and/or (c) a chromosome interval on chromosome 16 defined by and including base pair (bp) position 31292707 (SY0090) to base pair (bp) position 33324409 (SY3126), thereby identifying and/or selecting a BSR resistant soybean plant or part thereof.

In some embodiments, a method of identifying and/or selecting a BSR resistant soybean plant or part thereof is provided, the method comprising: detecting, in said soybean plant or part thereof, the presence of a marker associated with BSR resistance in a soybean plant, wherein said marker is located within a chromosomal interval comprising, consisting essentially of, or consisting of a chromosome interval on chromosome 16 defined by and including markers Sat_350 (physical position 30036787) and Satt431 (physical position 35718476), thereby identifying and/or selecting a BSR resistant soybean plant or part thereof.

In some embodiments of the present invention, a method of identifying and/or selecting a brown stem rot (BSR) resistant soybean plant or part thereof is provided, the method comprising detecting, in said soybean plant or part thereof, at least one allele of a marker locus that is associated with BSR resistance in a soybean plant, wherein said one or more marker locus is located within a chromosome interval comprising, consisting essentially of, or consisting of (a) a chromosome interval on chromosome 16 defined by and including base pair (bp) position 31292707 (SY0090) to base pair (bp) position 31869001 (SY0871); (b) a chromosome interval on chromosome 16 defined by and including base pair (bp) position 31869001 (SY0871) to base pair (bp) position 33324409 (SY3126); and/or (c) a chromosome interval on chromosome 16 defined by and including base pair (bp) position 31292707 (SY0090) to base pair (bp) position 33324409 (SY3126), thereby identifying and/or selecting a BSR resistant soybean plant or part thereof. In some embodiments, each bp position described herein can be defined by an allele, which allele can be heterozygous or homozygous. Accordingly, in some embodiments, the allele at bp position 31292707 (SY0090) can be a G or a GG, the allele at bp position 31869001 (SY0871) can be a T or a TT, and/or the allele at bp position 33324409 can be a G or a GG, in any combination thereof. In representative embodiments, the allele at bp position 31292707 (SY0090) is GG, the allele at bp position 31869001 (SY0871) is TT and the allele at bp position 33324409 (SY3126) is GG.

In some embodiments of the present invention, a method is provided of identifying and/or selecting a brown stem rot (BSR) resistant soybean plant or part thereof, comprising: detecting, in said soybean plant or part thereof, the presence of a marker associated with BSR resistance in a soybean plant, wherein said marker is located within a chromosome interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, thereby identifying and/or selecting a BSR resistant soybean plant or part thereof. In some embodiments, the G allele at SY0090 can be homozygous, the T allele at SY0871 can be homozygous, and/or the G allele at SY3126 can be homozygous. In some embodiments, the detecting step can detect (a) a chromosome interval on chromosome 16 defined by and including a GG allele at SY0090 and a TT allele at SY0871; and (b) a chromosome interval on chromosome 16 defined by and including a TT allele at SY0871 and a GG allele at SY3126, thereby identifying and/or selecting a BSR resistant soybean plant or part thereof.

In some embodiments, a method of identifying and/or selecting a brown stem rot (BSR) resistant soybean plant or part thereof is provided, the method comprising: detecting, in said soybean plant or part thereof, the presence of a marker associated with BSR resistance in a soybean plant, wherein said marker is located within a chromosome interval comprising, consisting essentially of, or consisting of: a chromosome interval on chromosome 16 defined by and including a G allele at SY0090, a T allele at SY0871 and a G allele at SY3126, thereby identifying and/or selecting a BSR resistant soybean plant or part thereof. In some embodiments, the alleles defining the chromosome intervals can be independently heterozygous or homozygous. In some embodiments, the allele at SY0090 can be a G or a GG, the allele at SY0871 can be a T or a TT, and/or the allele at SY3126 can be a G or a GG, or any combination thereof. In some embodiments, the detecting, in said soybean plant or part thereof, comprises, consists essentially of, consists of detecting the presence of a marker associated with BSR resistance in a soybean plant, wherein said marker is located within a chromosome interval comprising, consisting essentially of, or consisting of a chromosome interval on chromosome 16 defined by and including a GG allele at SY0090, a TT allele at SY0871 and a GG allele at SY3126.

In some embodiments, a method of identifying and/or selecting a brown stem rot (BSR) resistant soybean plant or part thereof is provided, comprising: detecting, in said soybean plant or part thereof, the presence of a combination of markers associated with BSR resistance in a soybean plant, wherein said combination of markers comprises, consists essentially of, or consists of: (a) a T allele at SY0871 and a G allele at SY3126; (b) a T allele at SY0871 and a G allele at SY0090; (c) a G allele at SY3126 and a G allele at SY0090; and/or (d) a T allele at SY0871 and a G allele at SY3126 and a G allele at SY0090, thereby identifying and/or selecting a BSR resistant soybean plant or part thereof.

In some embodiments, the present invention provides a method of identifying and/or selecting a brown stem rot (BSR) resistant soybean plant or part thereof, comprising detecting, in said soybean plant or part thereof, the presence of a marker associated with BSR resistance, wherein said marker comprises, consists essentially of, or consists of: (a) a G allele at SY0090; (b) a T allele at SY0871; (c) a T allele at SY3126; and (d) any combination of (a) through (c) above, thereby identifying and/or selecting a BSR resistant soybean plant or part thereof. In some embodiments, the T allele at SY0871 is homozygous, the T allele at SY3126 is homozygous and/or the G allele at SY0090 is homozyogous.

In some embodiments, the alleles of said markers can be independently heterozygous or homozygous. In some embodiments, the allele at SY0090 can be a G or a GG, the allele at SY0871 can be a T or a TT, and/or the allele at SY3126 can be a G or a GG, or any combination thereof. In a representative embodiment, the detecting, in said soybean plant or part thereof, comprises, consists essentially of, or consists of detecting the presence of: a GG allele at SY0090, a TT allele at SY0871 and a GG allele at SY3126.

As described herein, methods for identifying and/or selecting a soybean plant or germplasm having BSR resistance can comprise detecting the presence of a marker or a combination of markers associated with BSR resistance. Any combination of the genetic markers of this invention can be used to identify and/or select a soybean plant or germplasm having BSR resistance.

The subject matter disclosed herein also relates to methods for producing BSR resistant soybean plants comprising detecting the presence of a marker allele or a locus associated with BSR resistance in a donor soybean plant according to the methods as described herein and transferring a nucleic acid sequence comprising at least one allele thus detected from the donor plant to a BSR susceptible soybean plant. The transfer of the nucleic acid sequence can be performed by any of the methods described herein and/or as known in the art.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example, a plant obtained by inbreeding.

The presently disclosed subject matter thus also provides methods for selecting a plant of the genus *Glycine* exhibiting resistance to BSR comprising detecting in the plant the presence of one or more genetic markers associated with BSR resistance as defined herein. In an exemplary embodiment of the presently disclosed methods for selecting such a plant, the method comprises providing a sample of genomic DNA from a soybean plant; and (b) detecting in the sample of genomic DNA at least one genetic marker associated with BSR resistance as described herein. In some embodiments, the detecting can comprise detecting one or more SNPs, a combination of SNPs (e.g., haplotype), and/or SNPs located in chromosome intervals that are associated with BSR resistance.

The providing of a sample of genomic DNA from a soybean plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, an allele at a SNP site. In exemplary embodiments of this invention, nucleotide sequences comprising the genetic markers (SNPs) are provided (SEQ ID NO:1 (SY3126), SEQ ID NO:6 (SY0871), SEQ ID NO:11 (SY0090)), along with probes (SEQ ID NO:4 (SY3126; C allele), SEQ ID NO:5 (SY3126; G allele), SEQ ID NO:9 (SY0871; T allele), SEQ ID NO:10 (SY0871; A allele), SEQ ID NO:14 (SY0090; A allele), SEQ ID NO:15 (SY0090; G allele)) and primers (SEQ ID NOs:2 and 3 (SY3126); SEQ ID NOs:7 and 8 (SY0871); SEQ ID NOs:12 and 13 (SY0090).

In some embodiments of this invention, a method is provided, said method comprising the transfer by introgression of the nucleic acid sequence from a BSR resistant donor soybean plant into a BSR susceptible recipient soybean plant by crossing the plants. This transfer can be accomplished by using traditional breeding techniques. Loci associated with BSR resistance are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode the desired trait. As disclosed herein, such identification and selection is based on selection of one or more SNP alleles of this invention or markers associated therewith. MAB can also be used to develop near-isogenic lines (NIL) harboring one or more BSR resistance alleles of interest, allowing a more detailed study of an effect of such allele(s), and is also an effective method for development of backcross inbred line (BIL) populations. Soybean plants developed according to these embodiments can in some embodiments derive a majority of their traits from the recipient plant and derive BSR resistance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with BSR resistance into a BSR susceptible recipient soybean plant. For example, inbred BSR resistant soybean plant lines can be developed using the techniques of recurrent selection and backcrossing, selfing, and/or dihaploids, or any other technique used to make parental lines. In a method of recurrent selection and backcrossing, BSR resistance can be introgressed into a target recipient plant (the recurrent parent) by crossing the recurrent parent with a first donor plant, which differs from the recurrent parent and is referred to herein as the "non-recurrent parent." The recurrent parent is a plant that is BSR susceptible or has a low level of BSR resistance and, in some embodiments, comprises commercially desirable characteristics, such as, but not limited to disease and/or insect resistance, valuable nutritional characteristics, valuable abiotic stress tolerance (including, but not limited to, drought tolerance, salt tolerance), and the like. In some embodiments, the non-recurrent parent exhibits BSR resistance and comprises a nucleic acid sequence that is associated with BSR resistance. The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as are known in the art. Alternatively, instead of using bioassays, MAB can be performed using one or more of the hereinbefore described molecular markers, hybridization probes, or polynucleotides to identify those progeny that comprise a nucleic acid sequence associated with BSR resistance. Also, MAB can be used to confirm the results obtained from the quantitative bioassays. In some embodiments, the markers defined herein are suitable to select proper offspring plants by genotypic screening.

Following screening, the F1 hybrid plants that exhibit a BSR resistance phenotype or, in some embodiments, the genotype, and thus comprise the requisite nucleic acid sequence associated with BSR resistance, can then be selected and backcrossed to the recurrent parent for one or more generations in order to allow for the soybean plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype may be difficult to assay or occurs at a late stage in plant development. Since DNA marker assays are less laborious and take up less physical space than field phenotyping, much larger populations can be assayed, increasing the chances of finding a recombinant plant with the target segment from the donor line moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the soybean genome containing increasing densities of public soybean markers has facilitated soybean genetic mapping and MAS. See, e.g. soybeanbreederstoolbox.org, which can be found on the SoyBase website (soybase.org).

Of all the molecular marker types, SNPs are the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants, in* PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with BSR resistance. Thus, in some embodiments, the present invention relates to methods for producing soybean plants having a BSR resistance associated allele, comprising detecting the presence of at least one allele associated with BSR resistance in a donor soybean plant as described herein, crossing the donor soybean plant with a second soybean plant or germplasm, and detecting in the progeny plant(s) the presence of said at least one allele associated with BSR resistance, thereby transferring the at least one allele associated with BSR resistance thus detected from the donor soybean plant to the second soybean plant and thus producing a soybean plant (e.g., progeny plant) having BSR resistance. In some embodiments, the second soybean plant is BSR susceptible. The transfer of the allele associated with BSR resistance can be performed by any of the methods described herein.

Therefore, in some embodiments of the present invention, a method of producing a brown stem rot (BSR) resistant soybean plant is provided, the method comprising: detecting, in a soybean germplasm, the presence of a marker associated with BSR resistance in a soybean plant, wherein said one or more marker locus is located within a chromosome interval selected from the group consisting of: (a) a chromosome interval on chromosome 16 defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c), a chromosome interval on chromosome 16 defined by and including base pair (bp) position 31,292,707 (SY0090) to base pair (bp) position 33,324,409 (SY3126), and producing a soybean plant from said soybean germplasm, thereby producing a BSR resistant soybean plant or part thereof.

In some embodiments, a method of producing a brown stem rot (BSR) resistant soybean plant is provided, the method comprising: detecting, in a soybean germplasm, the presence of a marker associated with BSR resistance in a soybean plant, wherein said marker is located within a chromosome interval comprising, consisting essentially of, or consisting of a chromosome interval on chromosome 16 defined by and including markers Sat_350 (physical position 30036787) and Satt431 (physical position 35718476), and producing a plant from said germplasm, thereby producing a BSR resistant soybean plant.

In some embodiments of the methods of producing BSR resistant soybean plants, the base pair positions defining the chromosome intervals can comprise alleles, which can be independently heterozygous or homozygous. Thus, in some embodiments, the allele at bp position 31292707 (SY0090) can be a G or a GG, the allele at bp position 31869001 (SY0871) can be a T or a TT, and/or the allele at bp position 33,324,409 (SY3126) can be a G or a GG, in any combination thereof. In representative embodiments, the allele at bp position 31292707 (SY0090) is GG, the allele at bp position 31869001 (SY0871) is a TT, and the allele at bp position 33,324,409 (SY3126) is a GG.

In some embodiments of the present invention, a method of producing brown stem rot (BSR) resistant soybean plant is provided, the method comprising: detecting, in a soybean germplasm, the presence of a marker associated with BSR resistance in a soybean plant, wherein said marker is located within a chromosome interval comprising, consisting essentially of, or consisting of a chromosome interval on chromosome 16 defined by and including a G allele at SY0090, a T allele at SY0871 and a G allele at SY3126, and producing a soybean plant from said soybean germplasm, thereby producing a brown stem rot (BSR) resistant soybean plant.

In some embodiments, the alleles defining the chromosome intervals can be independently heterozygous or homozygous. Thus, in some embodiments, the allele at bp position 31292707 (SY0090) can be a G or a GG, the allele at bp position 31869001 (SY0871) can be a T or a TT, and/or the allele at bp position 33,324,409 (SY3126) can be a G or a GG, in any combination thereof. In representative embodiments, the allele at bp position 31292707 (SY0090) is GG, the allele at bp position 31869001 (SY0871) is a TT, and the allele at bp position 33,324,409 (SY3126) is a GG.

In some embodiments, the present invention provides a method of producing a brown stem rot (BSR) resistant soybean plant, comprising: detecting, in a soybean germplasm, the presence of a marker associated with BSR resistance in a soybean plant, wherein said marker is located within a chromosome interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, and producing a soybean plant from said soybean germplasm, thereby producing a brown stem rot (BSR) resistant soybean plant. In some embodiments, the G allele at SY0090 can be homozygous, the T allele at SY0871 can be homozygous, and/or the G allele at SY3126 can be homozygous. In some embodiments, the detecting step, in said soybean germplasm, comprises detecting the presence of: (a) a chromosome interval on chromosome 16 defined by and including a GG allele at SY0090 and a TT allele at SY0871; and (b) a chromosome interval on chromosome 16 defined by and including a TT allele at SY0871 and a GG allele at SY3126.

In some embodiments, a method of producing a brown stem rot (BSR) resistant soybean plant is provided, the method comprising: detecting, in a soybean germplasm, the presence of a combination of markers associated with BSR resistance in a soybean plant, wherein said combination of markers comprises, consists essentially of, or consists of (a) a G allele at SY0090 and a T allele at SY0871; (b) a T allele at SY0871 and a G allele at SY3126; (c) a G allele at SY0090 and a G allele at SY3126; and/or (d) a G allele at SY0090 and a T allele at SY0871 and a G allele at SY3126, and producing a soybean plant from said soybean germplasm, thereby producing a BSR resistant soybean plant.

In some embodiments, the invention provides a method of producing a brown stem rot (BSR) resistant soybean plant, comprising: detecting, in a soybean germplasm, the presence of one or more markers associated with BSR resistance in a soybean plant, wherein said marker comprises, consists essentially of, or consists of: (a) an G allele at SY0090; (b) a T allele at SY087a; (c) a G allele at Sy3126; and (d) any combination of (a) through (c) above, and producing a soybean plant from said soybean germplasm, thereby producing a BSR resistant soybean plant.

In some embodiments, the alleles of said markers (e.g., SY SY0090, SY0871, SY3126) can be independently homozygous or heterozygous. Thus, in some embodiments, the allele at SY0090 can be G or GG, the allele at SY0871 can be T or TT, the allele at and/or the allele at SY3126 can be G or GG, or any combination thereof. In some embodiments, the detecting in a soybean germplasm, comprises detecting the presence of: (a) a GG allele at SY0090, a TT allele at SY0871 and a GG allele at SY3126.

In some embodiments, a method of selecting a brown stem rot (BSR) resistant soybean plant and/or germplasm is provided, the method comprising: crossing a first soybean plant or germplasm with a second soybean plant or germplasm, wherein said first soybean plant or germplasm comprises within its genome a marker associated with BSR resistance in a soybean plant, wherein said marker is located within a chromosomal interval comprising, consisting essentially of, or consisting of (a) a chromosome interval on chromosome 16 defined by and including markers Satt_350 (physical position 30036787) and Satt431 (physical position 35718476), and producing a plant from said germplasm, thereby producing a BSR resistant soybean plant and selecting a progeny soybean plant or germplasm that comprises said marker within its genome, thereby selecting a BSR resistant soybean plant and/or germplasm.

In some embodiments, a method of selecting a brown stem rot (BSR) resistant soybean plant and/or germplasm is provided, the method comprising: crossing a first soybean plant or germplasm with a second soybean plant or germplasm, wherein said first soybean plant or germplasm comprises within its genome one or more markers or one or more marker loci associated with BSR resistance in a soybean plant, wherein said marker(s) and/or marker loci are located within a chromosomal interval selected from the group consisting of (a) a chromosome interval on chromosome 16 defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c) a chromosome interval on chromosome 16 defined by and including base pair (bp) position 31,292,707 (SY0090) to base pair (bp) position 33,324,409 (SY3126), and selecting a progeny soybean plant or germplasm that comprises said marker within its genome, thereby selecting a BSR resistant soybean plant or germplasm. In some embodiments, bp position 31,292,707 (SY0090) can comprise a G allele, bp position 31,869,001 (SY0871) can comprise a T allele, and/or bp position 33,324,409 (SY3126) can comprise a G allele. In some embodiments, thee G allele at bp position 31,292,707 (SY0090) is homozygous, the T allele at bp position 31,869,001 (SY0871) is homozygous and/or the G allele at bp position 33,324,409 (SY3126) is homozygous.

In some embodiments, a method of selecting a brown stem rot (BSR) resistant soybean plant and/or germplasm is provided, the method comprising: crossing a first soybean plant or germplasm with a second soybean plant or germplasm, wherein said first soybean plant or germplasm comprises within its genome a marker associated with BSR resistance in a soybean plant, wherein said marker is located within a chromosomal interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, and selecting a progeny soybean plant or germplasm that comprises said marker within its genome, thereby selecting a BSR resistant soybean plant or germplasm. In some embodiments, the G allele at SY0090 can be homozygous, the T allele at SY0871 can be homozygous, and/or the G allele at SY3126 can be homozygous. In some embodiments, the marker is located within (a) a chromosome interval on chromosome 16 defined by and including a GG allele at SY0090 and a TT allele at SY0871; and (b) a chromosome interval on chromosome 16 defined by and including a TT allele at SY0871 and a GG allele at SY3126.

In some embodiments, the invention provides a method of selecting a brown stem rot (BSR) resistant soybean plant and/or germplasm, comprising: crossing a first soybean plant or germplasm with a second soybean plant or germplasm, wherein said first soybean plant or germplasm comprises within its genome a combination of genetic markers associated with BSR resistance in a soybean plant, the combination of genetic markers comprising, consisting essentially of, or consisting of: (a) a T allele at SY0871 and a G allele at SY3126 (b) a T allele at SY0871 and a G allele at SY0090; (c) a G allele at SY3126 and a G allele at SY0090; and/or (d) a T allele at SY0871 and a G allele at SY3126 and a G allele at SY0090, and selecting a progeny soybean plant or germplasm that comprises said marker within its genome, thereby selecting a BSR resistant soybean plant and/or germplasm.

In some embodiments, a method of selecting a brown stem rot (BSR) resistant soybean plant and/or germplasm is provided, the method comprising: crossing a first soybean plant or germplasm with a second soybean plant or germplasm, wherein said first soybean plant or germplasm comprises within its genome a marker associated with BSR resistance in a soybean plant, wherein said marker is selected from the group consisting of: (a) a G allele at SY0090; (b) a T allele at SY0871; (c) a G allele at SY3126; and (d) any combination of (a) through (c) above; and selecting a progeny soybean plant or germplasm that comprises said marker within its genome, thereby selecting a BSR resistant soybean plant and/or germplasm.

In some embodiments, said allele at SY0090, at SY00871, and/or at SY3126 can be independently heterozygous or homozygous. Thus, in some embodiments, the allele at SY0090 can be a G or a GG, the allele at SY0871 can be T or a TT, and/or the allele at SY3126 can be a G or a GG, or any combination thereof. In representative embodiments, the combination of genetic markers can comprise a GG at SY0090, a TT at SY0871 and a GG at SY3126.

In some embodiments, the second soybean plant or germplasm of this invention is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

In some embodiments of this invention, a method of introgressing a genetic marker associated with brown stem rot (BSR) resistance into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with BSR resistance in a soybean plant, wherein said marker is located within a chromosome interval on chromosome 16 defined by and including markers Sat_350 (physical position 30036787) and Satt431 (physical position 35718476), and producing a BSR resistant soybean plant or germplasm comprising said genetic marker associated with BSR resistance in the genetic background of the recurrent parent, thereby introgressing the genetic marker associated with BSR resistance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with brown stem rot (BSR) resistance into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with BSR resistance in a soybean plant, wherein said marker is located within a chromosome interval selected from the group consisting of: (a) a chromosome interval on chromosome 16 defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c) a chromosome interval on chromosome 16 defined by and including base pair (bp) position 31,292,707 (SY0090) to base pair (bp) position 33,324,409 (SY3126), and producing a BSR resistant soybean plant or germplasm comprising said genetic marker associated with BSR resistance in the genetic background of the recurrent parent, thereby introgressing the genetic marker associated with BSR resistance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with brown stem rot (BSR) resistance in a soybean plant into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with BSR resistance in a soybean plant, wherein said marker is located within a chromosomal interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, thereby producing a BSR resistant soybean plant or germplasm comprising said genetic marker associated with BSR resistance in the genetic background of the recurrent parent, thereby introgressing the genetic marker associated with BSR resistance into a genetic background lacking said marker.

In some embodiments, the present invention provides a method of introgressing a genetic marker associated with brown stem rot (BSR) resistance in a soybean plant into a genetic background lacking said marker, the method comprising: crossing a donor soybean plant comprising said marker with a recurrent parent soybean plant that lacks said marker; and backcrossing progeny soybean plants comprising said marker with the recurrent parent soybean plant, wherein said progeny soybean plants are identified by detecting in their genome the presence of a combination of markers associated with BSR resistance in a soybean plant, wherein said combination of markers selected from the group consisting of: (a) a T allele at SY0871 and a G allele at SY3126; (b) a T allele at SY0871 and a G allele at SY0090; (c) a G allele at SY3126 and a G allele at SY0090; and (d) a T allele at SY0871 and a G allele at SY3126 and a G allele at SY0090, thereby producing a BSR resistant soybean plant or germplasm comprising said genetic marker associated with BSR resistance in the genetic background of the recurrent parent soybean plant, thereby introgressing the genetic marker associated with BSR resistance into a genetic background lacking said marker.

In some embodiments of this invention, a method of introgressing a genetic marker associated with brown stem rot (BSR) resistance in a soybean plant into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with BSR resistance in a soybean plant, wherein said marker comprises, consists essentially of, or consists of: (a) a G allele at SY0090; (b) a T allele at SY0871; (c) a G allele at SY3126; and (d) any combination of (a) through (c) above, thereby producing a BSR resistant soybean plant or germplasm comprising said genetic marker associated with BSR resistance in the genetic background of the recurrent parent, thereby introgressing the genetic marker associated with BSR resistance into a genetic background lacking said marker.

In embodiments of the invention described above, the alleles at base pair positions defining the chromosomal intervals comprising markers associated with BSR resistance and the alleles of the markers associated with BSR resistance can be independently heterozygous or homozygous. Thus, in some embodiments, the methods of introgressing comprise, consist essentially of, or consist of a G or a GG at base pair position SY0090; a T or a TT at base pair position SY0871; and/or a G or a GG at base pair position SY3126. In representative embodiments, the allele at bp position SY0090 is GG, the allele at bp position SY0871 is TT, and the allele at bp position SY3126 is GG.

In further embodiments of this invention, the marker alleles associated with frogeye leaf spot (FLS) resistance are as set forth in Table 2. In some embodiments of this invention, the marker allele(s) associated with frogeye leaf spot resistance as set forth in Table 2 can be located in (a) a chromosome interval on chromosome 16 (as used herein, "chromosome 16" can also mean "chromosome J") defined by and including base pair (bp) position 31,292,707 (SY0090) to base pair (bp) position 31,869,001 (SY0871); (b) a chromosome interval on chromosome 16 defined by and including base pair (bp) position 31,869,001 (SY0871) to base pair (bp) position 33,324,409 (SY3126); and (c) a chromosome interval on chromosome 16 defined by and including base pair (bp) position 31,292,707 (SY0090) to base pair (bp) position 33,324,409 (SY3126). In some embodiments, bp position 31,292,707 (SY0090) comprises a G allele, bp position 31,869,001 (SY0871) comprises a T allele, and/or bp position 33,324,409 (SY3126) comprises a G allele. In further embodiments, the G allele at bp position 31,292,707 (SY0090) can be homozygous, the T allele at bp position 31,869,001 (SY0871) can be homozygous, and/or the G allele at bp position 33,324,409 (SY3126) can be homozygous. As would be understood by one of skill in the art, additional chromosomal intervals can be defined by the SNP markers provided herein in Table 2.

In some embodiments, a marker allele(s) associated with FLS resistance can be located in a chromosome interval defined by and including (a) a chromosome interval on chromosome 16 (chromosome J) defined by and including markers Sat244 and Satt547.

In some embodiments, a genetic marker of this invention as set forth in Table 2 is associated with FLS resistance, wherein the genetic marker includes but is not limited to: (a) an A allele at SY3122; (b) a D (deletion) allele at SY0141; (c) an A allele at SY3124; (d) an AA allele at SY3122; (e) a DD allele at SY0141; (f) an AA allele at SY3124, and any combination of (a) through (f) above. Nonlimiting examples of combinations of this invention include (a) an A allele at SY3122 and a D allele at SY0141; (b) an A allele at SY3122 and an A allele at SY3124; (c) a D allele at SY0141 and an A allele at SY3124; and (d) an A allele at SY3122 and a D allele at SY0141 and an A allele at SY3124.

Accordingly, this invention further provides methods of identifying, selecting, and/or producing a frogeye leaf stem (FLS) resistant soybean plant or part thereof, comprising: detecting, in said soybean plant or part thereof, the presence of a combination of genetic markers associated with FLS resistance in a soybean plant, as described herein. In further embodiments, the marker can comprise, consist essentially of or consist of any marker linked to the aforementioned markers. That is, any genetic marker that is in linkage disequilibrium with any of the aforementioned markers (SNPs, chromosome intervals and/or combinations of markers (haplotypes)) may also be used to identify, select and/or produce a soybean plant having FLS resistance. Linked markers may be determined, for example, by using resources available on the SoyBase website (soybase.org).

The present invention further provides that the detecting of a molecular marker can comprise the use of a nucleic acid probe having a nucleotide base sequence that is substantially complementary to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of an SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 90%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencing instruments. Such methods of detecting an amplified DNA fragment are not described here in detail as they are well known to those of ordinary skill in the art.

As shown in Table 2, some of the SNP markers of this invention are associated with FLS resistance. In some embodiments, as described herein, one marker or a combination of markers can be used to detect the presence of a FLS resistant plant. In some embodiments, a marker can be located within a chromosomal interval (QTL) or be present in the genome of the plant (e.g., as a haplotype as defined herein).

Thus, methods for identifying and/or selecting a soybean plant or germplasm comprising FLS resistance comprise detecting the presence of a genetic marker (e.g., SNP, SNP located in chromosomal interval (QTL) and/or combination of SNPs) associated with FLS resistance in a soybean plant or part thereof. The genetic marker can be detected in any sample taken from the soybean plant or from a soybean germplasm, including, but not limited to, the whole plant or germplasm or any part thereof (e.g., a seed, a leaf, a tissue culture, a cell, etc.).

Thus, in some embodiments, the present invention provides a method of identifying and/or selecting a frogeye leaf spot (FLS) resistant soybean plant or part thereof, comprising: detecting, in said soybean plant or part thereof, at least one allele of a marker locus that is associated with FLS resistance in a soybean plant, wherein said one or more marker locus is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), thereby identifying and/or selecting a FLS resistant soybean plant or part thereof. In some embodiments, bp position 33,267,437 (SY3122) can comprise an A allele, bp position 33,311,672 (SY0141) can comprise a D allele, and/or bp position 33,322,599 (SY3124) can comprise an A allele. In some embodiments, the A allele at bp position 33,267,437 (SY3122) can be homozygous, the D allele at bp position 33,311,672 (SY0141) can be homozygous, and/or the A allele at bp position 33,324,409 (SY3124) can be homozygous.

The present invention further provides a method of identifying and/or selecting a frogeye leaf spot (FLS) resistant soybean plant or part thereof, comprising: detecting, in said soybean plant or part thereof, the presence of a marker associated with FLS resistance in a soybean plant, wherein said marker is located within a chromosome interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, thereby identifying and/or selecting a FLS resistant soybean plant or part thereof. In some embodiments, the A allele at SY3122 can be homozygous, the D allele at SY0141 can be homozygous, and/or the A allele at SY3124 can be homozygous. In some embodiments, the detecting, in said soybean plant or part thereof, can comprise detecting the presence of: (a) a chromosome interval on chromosome 16 defined by and including an AA allele at SY3122 and a DD allele at SY0141; and (b) a chromosome interval on chromosome 16 defined by and including a DD allele at SY0141 and an AA allele at SY3124, thereby identifying and/or selecting a FLS resistant soybean plant or part thereof.

In some embodiments, the present invention provides a method of identifying and/or selecting a frogeye leaf spot (FLS) resistant soybean plant or part thereof, comprising: detecting, in said soybean plant or part thereof, the presence of a marker associated with FLS resistance, wherein said marker is selected from the group consisting of: (a) an A allele at SY3122; (b) a D allele at SY0141; (c) an A allele at SY3124; and (d) any combination of (a) through (c) above, thereby identifying and/or selecting a FLS resistant soybean plant or part thereof. In some embodiments, the A allele at SY3122 can be homozygous, the D allele at SY0141 can be homozygous, and/or the A allele at SY3124 can be homozygous. In some embodiments, the detecting, in said soybean plant or part thereof, can comprise detecting the presence of: (a) an AA allele at SY3122; (b) a DD allele at SY0141; and (c) an AA allele at SY3124.

In further embodiments, the present invention provides a method of identifying and/or selecting a frogeye leaf spot (FLS) resistant soybean plant or part thereof, comprising: detecting, in said soybean plant or part thereof, the presence of a combination of markers associated with FLS resistance in a soybean plant, wherein said combination of markers is selected from the group consisting of: (a) an A allele at SY3122 and a D allele at SY0141 (b) an A allele at SY3122 and an A allele at SY3124; (c) a D allele at SY0141 and an A allele at SY3124; and (d) an A allele at SY3122 and a D allele at SY0141 and an A allele at SY3124, thereby identifying and/or selecting a FLS resistant soybean plant or part thereof. In some embodiments, the A allele at SY3122 can be homozygous, the D allele at SY0141 can be homozygous, and/or the A allele at SY3124 can be homozygous.

In some embodiments, the present invention provides a method of identifying and/or selecting a frogeye leaf spot (FLS) resistant soybean plant or part thereof, comprising: detecting, in said soybean plant or part thereof, at least one allele of a marker locus that is associated with FLS resistance in a soybean plant, wherein said one or more marker locus is located within a chromosome interval on chromosome 16 defined by and including markers Sat244 and Satt547.thereby producing a FLS resistant soybean plant or part thereof.

In some embodiments, the present invention provides a method of producing a frogeye leaf spot (FLS) resistant soybean plant, comprising: detecting, in said soybean plant or part thereof, at least one allele of a marker locus that is associated with FLS resistance in a soybean plant, wherein said one or more marker locus is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), thereby producing a FLS resistant soybean plant or part thereof. In some embodiments, bp position 33,267,437 (SY3122) can comprise an A allele, bp position 33,311,672 (SY0141) can comprise a D allele, and/or bp position 33,322,599 (SY3124) can comprise an A allele. In some embodiments, the A allele at bp position 33,267,437 (SY3122) can be homozygous, the D allele at bp position 33,311,672 (SY0141) can be homozygous, and/or the A allele at bp position 33,322,599 (SY3124) can be homozygous.

In some embodiments, the present invention provides a method of producing a frogeye leaf spot (FLS) resistant soybean plant, comprising: detecting, in a soybean germplasm, the presence of a marker associated with FLS resistance in a soybean plant, wherein said marker is located within a chromosome interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, and producing a soybean plant from said soybean germplasm, thereby producing a frogeye leaf spot (FLS) resistant soybean plant. In some embodiments, the A allele at SY3122 can be homozygous, the D allele at SY0141 can be homozygous, and/or the A allele at SY3124 can be homozygous. In some embodiments, the detecting, in said soybean germplasm, comprises detecting the presence of: (a) a chromosome interval on chromosome 16 defined by and including an AA allele at SY3122 and a DD allele at SY0141; and (b) a chromosome interval on chromosome 16 defined by and including a DD allele at SY0141 and an AA allele at SY3124.

In some embodiments, the present invention provides a method of producing a frogeye leaf spot (FLS) resistant soybean plant, comprising: detecting, in a soybean germplasm, the presence of a combination of markers associated with FLS resistance in a soybean plant, wherein said combination of markers is selected from the group consisting of: (a) an A allele at SY3122 and a D allele at SY0141; (b) a D allele at SY0141 and an A allele at SY3124; (c) an A allele at SY3122 and an A allele at SY3124; and (d) an A allele at SY3122 and a D allele at SY0141 and an A allele at SY3124, and producing a soybean plant from said soybean germplasm, thereby producing a FLS resistant soybean plant. In some embodiments, the A allele at SY3122 can be homozygous, the D allele at SY0141 can be homozygous, and/or the A allele at SY3124 can be homozygous.

In some embodiments, the present invention provides a method of producing a frogeye leaf spot (FLS) resistant soybean plant, comprising: detecting, in a soybean germplasm, the presence of a marker associated with FLS resistance in a soybean plant, wherein said marker is selected from the group consisting of: (a) an A allele at SY3122; (b) a D allele at SY0141; (c) an A allele at SY3124; and (d) any combination of (a) through (c) above, and producing a soybean plant from said soybean germplasm, thereby producing a FLS resistant soybean plant. In some embodiments, the A allele at SY3122 can be homozygous, the D allele at SY0141 can be homozygous, and/or the A allele at SY3124 can be homozygous. In some embodiments, the detecting, in a soybean germplasm, comprises detecting the presence of: (a) an AA allele at SY3122; (b) a DD allele at SY0141; and (b) an AA allele at SY3124.

In some embodiments, the present invention provides a method of producing a frogeye leaf spot (FLS) resistant soybean plant or part thereof, comprising: detecting, in said soybean plant or part thereof, at least one allele of a marker locus that is associated with FLS resistance in a soybean plant, wherein said one or more marker locus is located within a chromosome interval on chromosome 16 defined by and including markers Sat244 and Satt547, thereby producing a FLS resistant soybean plant or part thereof.

In a further embodiment, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), and selecting a progeny soybean plant or germplasm that comprises said marker within its genome, thereby selecting a FLS resistant soybean plant or germplasm. In some embodiments, bp position 33,267,437 (SY3122) can comprise an A allele, bp position 33,311,672 (SY0141) can comprise a D allele, and/or bp position 33,322,599 (SY3124) can comprise an A allele. In some embodiments, the A allele at bp position 33,267,437 (SY3122) can be homozygous, the D allele at bp position 33,311,672 (SY0141) can be homozygous and/or the A allele at bp position 33,322,599 (SY3124) can be homozygous.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is located within a chromosome interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, and selecting a progeny soybean plant or germplasm that comprises said marker within its genome, thereby selecting a FLS resistant soybean plant or germplasm. In some embodiments, the A allele at SY3122 can be homozygous, the D allele at SY0141 can be homozygous, and/or the A allele at SY3124 can be homozygous. In some embodiments, said marker is located within (a) a chromosome interval on chromosome 16 defined by and including an AA allele at SY3122 and a DD allele at SY0141; and (b) a chromosome interval on chromosome 16 defined by and including a DD allele at SY0141 and an AA allele at SY3124.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a combination of genetic markers associated with FLS resistance in a soybean plant, the combination of genetic markers selected from the group consisting of: (a) an A allele at SY3122 and a D allele at SY0141; (b) a D allele at SY0141 and an A allele at SY3124; (c) an A allele at SY3122 and an A allele at SY3124; and (d) an A allele at SY3122 and a D allele at SY0141 and an A allele at SY3124, and selecting a progeny soybean plant or germplasm that comprises said marker within its genome, thereby selecting a FLS resistant soybean plant or germplasm. In some embodiments, the A allele at SY3122 can be homozygous, the D allele at SY0141 can be homozygous, and/or the A allele at SY3124 can be homozygous.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is selected from the group consisting of: (a) an A allele at SY3122; (b) a D allele at SY0141; (c) an A allele at SY3124; and (d) any combination of (a) through (c) above, and selecting a progeny soybean plant or germplasm that comprises said marker within its genome, thereby selecting a FLS resistant soybean plant or germplasm. In some embodiments, the A allele at SY3122 can be homozygous, the D allele at SY0141 can be homozygous, and/or the A allele at SY3124 can be homozygous. In some embodiments, the combination of genetic markers can be (a) an AA allele at SY3122; (b) a DD allele at SY0141; and (c) an AA allele at SY3124.

In some embodiments, the present invention provides a method of selecting a frogeye leaf spot (FLS) resistant soybean plant or germplasm, comprising: crossing a first soybean plant or germplasm with a second soybean plant or germplasm, wherein said first soybean plant or germplasm comprises within its genome a marker associated with FLS resistance in a soybean plant, wherein said marker is located within a chromosome interval on chromosome 16 defined by and including markers Sat244 and Satt547; and selecting a progeny soybean plant or germplasm that comprises said marker within its genome, thereby selecting a FLS resistant soybean plant or germplasm.

The present invention further provides a FLS resistant soybean plant or germplasm identified, produced or selected by any of the methods described herein.

Also provided herein is a seed produced by a FLS resistant soybean plant identified, produced or selected by any of the methods described herein.

In addition, the methods of producing an FLS resistant soybean plant described above can further comprise the steps of (a) crossing the selected progeny soybean plant or germplasm that comprises said marker within its genome with itself or another soybean plant to yield additional progeny soybean plants comprising the marker within their genome; and (b) repeating the crossing step of (a) from 0 to about 7 times to generate further progeny soybean plants comprising the marker within their genome. In some embodiments, the selected progeny soybean plant or germplasm can be crossed with a transgenic soybean plant comprising at least one nucleotide sequence of interest in its genome to yield a progeny soybean plant comprising the marker and the at least one nucleotide sequence of interest within its genome.

In some embodiments of this invention, a method of introgressing a genetic marker associated with frogeye leaf spot (FLS) resistance into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with FLS resistance in a soybean plant, wherein said marker is located within a chromosome interval on chromosome 16 defined by and including markers Sat244 and Satt547 and producing a FLS resistant soybean plant or germplasm comprising said genetic marker associated with FLS resistance in the genetic background of the recurrent parent, thereby introgressing the genetic marker associated with FLS resistance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with frogeye leaf spot (FLS) resistance into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with FLS resistance in a soybean plant, wherein said marker is located within a chromosome interval selected from the group consisting of: (a) a chromosome interval on chromosome 16 defined by and including base pair (bp) position 33,267,437 (SY3122) to base pair (bp) position 33,311,672 (SY0141); (b) a chromosome interval on chromosome 16 defined by and including base pair (bp) position 33,311,672 (SY0141) to base pair (bp) position 33,322,599 (SY3124); and (c) a chromosome interval on chromosome 16 defined by and including base pair (bp) position 33,267,437 (SY3122) to base pair (bp) position 33,322,599 (SY3124), and producing a FLS resistant soybean plant or germplasm comprising said genetic marker associated with FLS resistance in the genetic background of the recurrent parent, thereby introgressing the genetic marker associated with FLS resistance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with brown stem rot (BSR) resistance in a soybean plant into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with BSR resistance in a soybean plant, wherein said marker is located within a chromosomal interval selected from the group consisting of: (a) a chromosome interval on chromosome 16 defined by and including an A allele at SY3122 and a D allele at SY0141; (b) a chromosome interval on chromosome 16 defined by and including a D allele at SY0141 and an A allele at SY3124; and (c) a chromosome interval on chromosome 16 defined by and including an A allele at SY3122 and an A allele at SY3124, thereby producing a FLS resistant soybean plant or germplasm comprising said genetic marker associated with FLS resistance in the genetic background of the recurrent parent, thereby introgressing the genetic marker associated with BSR resistance into a genetic background lacking said marker.

In some embodiments, the present invention provides a method of introgressing a genetic marker associated with frogeye leaf stem (FLS) resistance in a soybean plant into a genetic background lacking said marker, the method comprising: crossing a donor soybean plant comprising said marker with a recurrent parent soybean plant that lacks said marker; and backcrossing progeny soybean plants comprising said marker with the recurrent parent soybean plant, wherein said progeny soybean plants are identified by detecting in their genome the presence of a combination of markers associated with FLS resistance in a soybean plant, wherein said combination of markers selected from the group consisting of: (a) an A allele at SY3122 and a D allele at SY0141 (b) an A allele at SY3122 and an A allele at SY3124; (c) a D allele at SY0141 and an A allele at SY3124; and (d) an A allele at SY3122 and a D allele at SY0141 and an A allele at SY3124, thereby producing a FLS resistant soybean plant or germplasm comprising said genetic marker associated with FLS resistance in the genetic background of the recurrent parent soybean plant, thereby introgressing the genetic marker associated with FLS resistance into a genetic background lacking said marker.

In some embodiments of this invention, a method of introgressing a genetic marker associated with brown stem rot (BSR) resistance in a soybean plant into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with BSR resistance in a soybean plant, wherein said marker comprises, consists essentially of, or consists of: (a) an A allele at SY3122; (b) a D allele at SY0141; (c) an A allele at SY3124; and (d) any combination of (a) through (c) above, thereby producing a FLS resistant soybean plant or germplasm comprising said genetic marker associated with FLS resistance in the genetic background of the recurrent parent, thereby introgressing the genetic marker associated with FLS resistance into a genetic background lacking said marker.

In embodiments of the invention described above, the alleles at base pair positions defining the chromosomal intervals comprising markers associated with FLS resistance and the alleles of the markers associated with FLS resistance can be independently heterozygous or homozygous. Thus, in some embodiments, the methods of introgressing comprise, consist essentially of, or consist of a D or a DD at base pair position SY0141; an A or an AA at base pair position SY3122; and/or an A or an AA at base pair position SY3124. In representative embodiments, the allele at bp position SY0141 is DD, the allele at bp position SY3122 is AA, and the allele at bp position SY3124 is AA.

As is well known in the art, the detecting of a genetic marker can in some embodiments comprise the use of one or more sets of primer pairs that can be used to produce one or more amplification products that are suitable for identifying, for example, an allele at a SNP site. In exemplary embodiments of this invention, nucleotide sequences comprising the genetic markers (SNPs) are provided (SEQ ID NO:16 (SY0141), SEQ ID NO:21 (SY3122), SEQ ID NO:26 (SY3124)), along with probes (SEQ ID NO:19 (SY0141; I allele), SEQ ID NO:20 (SY0141; D allele), SEQ ID NO:24 (SY3122; A allele), SEQ ID NO:25 (SY3122; T allele), SEQ ID NO:29 (SY3124; A allele), SEQ ID NO:30 (SY3124; G allele)) and primers (SEQ ID NOs:17 and 18 (SY0141); SEQ ID NOs:22 and 23 (SY3122); SEQ ID NOs:27 and 28 (SY3124).

The present invention provides soybean plants and germplasms having BSR and/or FLS resistance. As discussed above, the methods of the present invention can be utilized to identify, produce and/or select a soybean plant or germplasm having BSR and/or FLS resistance. In addition to the methods described above, a soybean plant or germplasm having BSR and/or FLS resistance may be produced by any method whereby a marker associated with BSR or FLS resistance in a soybean plant is introduced into the soybean plant or germplasm by such methods that include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having a genetic marker associated with BSR or FLS resistance, obtainable by the methods of the presently disclosed subject matter, are aspects of the presently disclosed subject matter. The soybean plant, or part thereof, or soybean germplasm of this invention having a genetic marker associated with BSR or FLS resistance can be heterozygous or homozygous for the genetic marker.

In some embodiments, the soybean plant or germplasm may be the progeny of a cross between an elite variety of soybean and a variety of soybean that comprises an allele associated with BSR or FLS resistance. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The soybean plant or germplasm may be the progeny of an introgression wherein the recurrent parent is an elite variety of soybean and the donor comprises a genetic marker associated (e.g., SNP, combination of SNPs, SNP located in a chromosome interval) with BSR or FLS resistance in a soybean plant as described herein.

The soybean plant or germplasm may be the progeny of a cross between a first elite variety of soybean (e.g., a tester line) and the progeny of a cross between a second elite variety of soybean (e.g., a recurrent parent) and a variety of soybean that comprises a genetic marker associated with BSR or FLS resistance in a soybean plant as described herein (e.g., a donor).

The soybean plant or germplasm may be the progeny of a cross between a first elite variety of soybean and the progeny of an introgression wherein the recurrent parent is a second elite variety of soybean and the donor comprises a genetic marker associated with BSR or FLS resistance in a soybean plant.

Another aspect of the presently disclosed subject matter relates to a method of producing seeds that can be grown into BSR and/or FLS resistant soybean plants. In some embodiments, the method comprises providing a BSR and/or FLS resistant soybean plant of this invention, crossing the BSR and/or FLS resistant soybean plant with another soybean plant, and collecting seeds resulting from the cross, which when planted, produce BSR and/or FLS resistant soybean plants.

Accordingly, the present invention provides improved soybean plants, seeds, and/or soybean tissue culture produced by the methods described herein.

In some embodiments, the presently disclosed subject matter provides methods for analyzing the genomes of soybean plants/germplasms to identify those that include desired markers associated with BSR and/or FLS resistance. In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs that initiate DNA polymerization by a DNA polymerase on a *Glycine max* nucleic acid template to generate a *Glycine max* amplicon. In some embodiments, the *Glycine max* marker amplicon corresponds to a *Glycine max* marker comprising a nucleotide sequence of any of SEQ ID NOs:1, 6, and 11. In view of the disclosure of SEQ ID NOs:1, 6, and 11 as being linked to BSR resistance loci, one of ordinary skill in the art would be aware of various techniques that could be employed to analyze the sequences of the corresponding soybean nucleic acids.

Furthermore, in some embodiments, the *Glycine max* marker amplicon corresponds to a *Glycine max* marker comprising a nucleotide sequence of any of SEQ ID NOs:16, 21, and 26. In view of the disclosure of SEQ ID NOs:16, 21, and 26 as being linked to FLS resistance loci, one of ordinary skill in the art would be aware of various techniques that could be employed to analyze the sequences of the corresponding soybean nucleic acids.

In addition to the markers for brown stem rot (BSR) described above, the methods of this invention can be applied to detect other markers associated with brown stem rot resistance, including but not limited to: A allele at bp position 3430300 (SY1632A); G allele at bp position 32526899 (SY0094C); T allele at bp position 12256147 (SY0802A); C allele at bp position 44461635 (SY0738A); A allele at bp position 35361509 (SY1001A); G allele at bp position 46041852 (SY0336B); C allele at bp position 15318355 (SY2513A); A allele at bp position 5385238 (SY2092A); C allele at bp position 569335 (SY0827A); C allele at bp position 42829778 (SY1591A); I allele at bp position 3964338 (SY1048A); G allele at bp position 5387449 (SY2093A); A allele at bp position 31863327 (SY3110); G allele at bp position 33537317 (SY0004A); G allele at bp position 35208490 (SY1044B); C allele at bp position 31154850 (SY0089B); T allele at by position 32896631 (SY3115); A allele at by position 31114052 (SY3106); T allele at bp position 37289212 (SY2843); C allele at bp position 32100265 (SY0096D); and/or G allele at bp position 33473999 (SY0099D), in any combination.

In another embodiment the invention comprises a method of identifying and/or selecting a brown stem rot (BSR) resistant soybean plant or part thereof, comprising: detecting, in said soybean plant or part thereof, the presence of a marker associated with BSR resistance in a soybean plant, wherein said marker is located within a chromosome interval selected from the group consisting of: (a) a chromosome interval on chromosome 16 defined by and including a G allele at SY0090 and a T allele at SY0871; (b) a chromosome interval on chromosome 16 defined by and including a T allele at SY0871 and a G allele at SY3126; and (c) a chromosome interval on chromosome 16 defined by and including a G allele at SY0090 and a G allele at SY3126, thereby identifying and/or selecting a BSR resistant soybean plant or part thereof. In some instances the G allele at SY0090 is homozygous, the T allele at SY0871 is homozygous, and/or the G allele at SY3126 is homozygous for the above mentioned method. In other instances the BSR resistant plants are detected for the presence of any one of or a combination of: (a) a chromosome interval on chromosome 16 defined by and including a GG allele at SY0090 and a TT allele at SY0871; and (b) a chromosome interval on chromosome 16 defined by and including a TT allele at SY0871 and a GG allele at SY3126.

Additionally, the invention contemplates a method of identifying and/or selecting a brown stem rot (BSR) resistant soybean plant or part thereof, comprising:detecting, in said soybean plant or part thereof, the presence of a combination of markers associated with BSR resistance in a soybean plant, wherein said combination of markers is selected from the group consisting of: (a) a T allele at SY0871 and a G allele at SY3126; (b) a T allele at SY0871 and a G allele at SY0090; (c) a G allele at SY3126 and a G allele at SY0090; and (d) a T allele at SY0871 and a G allele at SY3126 and a G allele at SY0090, thereby identifying and/or selecting a BSR resistant soybean plant or part thereof.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

That which is claimed:

1. A method of producing a frogeye leaf spot (FLS) resistant soybean plant, the method comprising the steps of:
   (a) isolating at least one nucleic acid from a soybean plant selected from a population of soybean plants;
   (b) detecting, in the nucleic acid of (a) at least one allele of a marker locus that is associated with FLS resistance in a soybean plant, wherein said marker locus is located within a chromosome interval on soybean chromosome 16 defined by and including base pair (bp) position 33,267,437 (SY3122) to base pair (bp) position 33,322,592 (SY3124), wherein by position 33,267,437 (SY3122) comprises an A allele and bp position 33,322,592 (SY3124) comprises an A allele;
   (c) selecting a first soybean plant from the soybean population of (a) based on the presence of the allele detected in (b);
   (d) crossing the first soybean plant of (c) with a second soybean plant not comprising in its genome the marker locus of (b);
   (e) collecting seed from the cross of (d); and
   (f) growing a progeny soybean plant from the seed of (e), wherein said progeny soybean plant comprises in its genome said marker locus associated with FLS resistance, thereby producing a FLS resistant soybean plant.

2. The method of claim 1, wherein the A allele at bp position 33,267,437 (SY3122) and the A allele at bp position 33,322,592 (SY3124) are homozygous.

3. The method of claim 1, wherein the detecting comprises detecting at least one allelic form of a polymorphic simple sequence repeat (SSR) or a single nucleotide polymorphism (SNP).

4. The method of claim 1, wherein the detecting comprises amplifying the marker locus or a portion of the marker locus and detecting the resulting amplified marker amplicon.

5. The method of claim 4, wherein the amplifying comprises: (a) admixing an amplification primer or amplification primer pair with a nucleic acid isolated from the first *Glycine max* plant or germplasm, wherein the primer or primer pair is complementary or partially complementary to at least a portion of the marker locus, and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon.

* * * * *

SEQUENCE LISTING

```
<160> NUMBER OF SEQ ID NOS: 30

<210> SEQ ID NO 1
<211> LENGTH: 2811
<212> TYPE: DNA
<213> ORGANISM: Glycine max
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (1686)..(1687)
<223> OTHER INFORMATION: n is a, c, g, or t
<220> FEATURE:
<221> NAME/KEY: misc_feature
<222> LOCATION: (1863)..(1863)
<223> OTHER INFORMATION: n is a, c, g, or t

<400> SEQUENCE: 1
ggaggaggaa gtgtaccgtc ccgacttggg aaccttccaa atttgctgaa gctttatctt      60
ggaggccgat catattatgg tggtgctctc aaaattgacg atggagatcg ttggctgtct     120
aatctcattt ctttaaccca tctttccttg gactccatat ctaatctcaa cacttctcat     180
agcttcctcc caatgattgc caagctacca aaacttagag aactaagttt aattcattgt     240
agcctttccg atcattttat cctttcattg aagccctcta aattcaattt ttctagttcc     300
ctttccatcc ttgatcttac ctggaacagc ttcacgtcat caacgatact ccagtggctg     360
tctgggtgtg ccagattctc gcttcaagaa ttgaacttaa gaggaaatca aatcaacggt     420
acgcttcctg acctttcaat attttctgcc ttgaaaagat tggatctttc agaaaatcaa     480
ttaaatggga aaattctaga nagtaccaaa ttgccacctc tgttggagtc tttgtcaatc     540
acttcaaaca ttttggaagg tggaattcca aaatcatttg ggaatgcatg tgctttgcgc     600
tcattggaca tgtcttataa tagcttgagt gaagagtttc caatgataat ccatcacttg     660
tctggatgtg ctagatattc attggaacga ttatatctag gcaagaatca aatcaatggt     720
acactacccg acctctcaat attctcatct ttaagagaat tatatctttc tggaaacaag     780
ctaaatggag agattcctaa agatattaaa tttccacctc aacttgagga actagatttg     840
caatcaaatt ccttaaaggg tgtgctcact gactatcatt cgctaacat gtctaantta     900 gacttcttgg agttatctga caactcttta ttggccttga catttagtcc aaattgggtt     960
ccaccgtttc agttgagcca cataggattg cgatcttgca aactaggtcc agtatttccc    1020
aaatggttgg agacacaaaa tcaatttggg gatattgaca tttcaaattc tggaatagaa    1080
```

```
gatatggttc caaagtggtt ttgggctaaa ttaacatttc gagaatccat ttcaatgaat    1140
atttcacaca ataatctcca tggtataatt ccaaattttc cactaaagaa tctttaccat    1200
tccctaattc ttggatcaaa tcaatttgat ggccctattc caccatttct tcgaggtttc    1260
ctgtttcttg atttatccaa aaataaattc tcagattctc tttcatttt atgtgcaaat     1320 ggtacagttg aaactttgta ccaattagac ctttcaaata atcgtttctc tggaaaaatt   1380
ccggactgtt ggaaccattt caagtcatta tcttatttgg acttgagtca caataatttt   1440
tcaggaagaa tacctacatc catgggatct cttcttcatc ttcaagcatt gctattgaga    1500
aacaacaact taacagatga gataccttc tccttgagga gttgcacaaa tctagtaatg     1560
ctagatattg cagaaaacaa attatcaggg ctcatccctg cttggattgg gagtgaatta    1620
caagagttgc aattttttaag tttgaaagaa aataatttcc atggaagttt accattgcaa   1680
atttgnnacc taagtaacat tcaactcttg gatctctcaa taaataacat gtctgggaaa    1740
attcctaaat gcataaaaaa atttacttca atgactcgaa aaacatcttc aggagattat    1800
caacttcatt catatcaggt caataccact tacacaaggg ttaaccaaac atatgatttg    1860
aangcactct tgatgtggaa aggttcagaa cgaatattca aaactaaagt gttactactt    1920
gtaaaaagca ttgatctctc aagcaatcac ttttctggag aaattccaca ggaaatagag    1980
aatttatttg gattggtttc attgaatta tcaagaaaca atttgatagg gaaaattccc     2040
tcaaaaattg gaaagctaac atcacttgaa tctcttgatt tgtcaagaaa ccagttggct    2100
ggttcaattc ctccgagtct tacacaaatt tatggcctcg gcgtgttaga tttgtcacat    2160
aaccatctaa ctggaaaaat tccagccagc acacagttac agagtttcaa tgcctcgagt    2220
tatgaagata atcttgatct ttgtggacag ccacttgaga aattttgtat tgatgggaga    2280
cctacacaaa aaccaaatgt tgaagttcaa satgacgaat tttcactttt caatcgtgaa    2340
ttttacatga gtatgacatt tggatttgtt ataagctttt ggatggtgtt tggctcaatc    2400
ttattcaagc gttcttggag acatgcctat ttcaagttct tgaacaatct atcagacaat    2460
atttatgtca aggtagcagt atttgctaat aaaaatgtcaa aggtgtatgg ctgaagctta   2520
actaggtaat aatattgcag ccctttcata tatatatata tatatatata gtttcttttg    2580
ctttcatata gttatatac atgaaagatt ccatatatat tataatttgg aattgtgaca     2640
gtaagatttc ataattttta actatttag tataataaat tttgaagaaa tattgaataa    2700
gttatattaa gattaattaa taatataaaa ttatattgtt actgtataat cattaaaatt   2760
atcattattg atgtataata agcctgaaac atcgttgatc tctattatta t            2811
```

```
<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gtattgatgg gagacctaca caa                                              23

<210> SEQ ID NO 3
<211> LENGTH: 20
<212> TYPE: DNA
<213> ORGANISM: Artificial Sequence
<220> FEATURE:
<223> OTHER INFORMATION: Primer
```

<400> SEQUENCE: 3
tgagccaaac accatccaaa                                              20

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
tgaagttcaa catgacg                                                 17

<210> SEQ ID NO 5
<211> LENGTH: 18
<212> TYPE: DNA
<213> ORGANISM: Artificial Sequence
<220> FEATURE:
<223> OTHER INFORMATION: Probe

<400> SEQUENCE: 5
ttgaagttca agatgacg                                                18

<210> SEQ ID NO 6
<211> LENGTH: 529
<212> TYPE: DNA
<213> ORGANISM: Glycine max

<400> SEQUENCE: 6
agaggaggta ccgaggccac ccctccggt catttcccgg gaacccgaac cagatctggg    60
tggtggagat ccacgttcta aagttgaaga cgatctagat atcggtgaag acctgttaaa  120
gatatcacag cgtcggaata ttgawgaaat tgacgaggac atccggagca gaggaagcaa  180
tggacctccc cataatactt ctgaagtaga ttcagttttg ggttcagatc gccgggcccc  240
aacaattcga tctgaagcaa ggcactcaag tgagggaaga agtgaaagct gggaaatcgg  300
gtctgaggtc cttgccaatt caactgtaac tgaaagcaga agctatgttg tatcaaagga  360
ggtgcgccaa aaacttgggg gttctttctg agatgtgggg tttcttagat attaaaaatg  420
gaaaaggaaa tggtgtttga tcagattata ggaatgggaa ttgaattgat tgaggcatta  480
agtacaaaac ttatttgatc ttttttttgtg gtaaggttag ctcttttgg              529

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gaggtccatt gcttcctctg ct                                           22

<210> SEQ ID NO 8
<211> LENGTH: 23
<212> TYPE: DNA
<213> ORGANISM: Artificial Sequence
<220> FEATURE:
<223> OTHER INFORMATION: Primer 2

<400> SEQUENCE: 8
tggtggagat ccacgttcta aag                                          23

```
<210> SEQ ID NO 9
<211> LENGTH: 17
<212> TYPE: DNA
<213> ORGANISM: Artificial Sequence
<220> FEATURE:
<223> OTHER INFORMATION: Probe 1

<400> SEQUENCE: 9
ctcgtcaatt tcatcaa                                                      17

<210> SEQ ID NO 10
<211> LENGTH: 17
<212> TYPE: DNA
<213> ORGANISM: Artificial Sequence
<220> FEATURE:
<223> OTHER INFORMATION: Probe

<400> SEQUENCE: 10
ctcgtcaatt tcttcaa                                                      17

<210> SEQ ID NO 11
<211> LENGTH: 429
<212> TYPE: DNA
<213> ORGANISM: Glycine max
<220> FEATURE:
<221> NAME/KEY: misc_feature
<222> LOCATION: (30)..(30)
<223> OTHER INFORMATION: n is a, c, g, or t

<400> SEQUENCE: 11
gattctcctc cagatttgaa agatccaggn tgacaaaaga gaacgaacct tctgggtcat        60
caaatagagg tctggtgaat tcattaaact caccaaagtt ggcttcaaag ttcaatgatg       120
agaaataatt gataggatca tcgctatcgc cttttrcatc catggcattt ggaacttcat       180
ttgcatttga aggatttgat ccaaaagtga agttcatgct ctgcaccttta ctgttgttct     240 ctttgctatc atgaatgggt gcctcagcta cccctgcccc tttagtgtca tccaaaggaa       300
tggctggtgc atgcccttgg aaaagagcaa tgtgcccaaa aagcttgtct ttcctagaaa       360
atgttgtgcc acacgaacag agccatttat ccttaccaca gtgtttttca tgagttttta     420
gatcagcca                                                              429

<210> SEQ ID NO 12
<211> LENGTH: 25
<212> TYPE: DNA
<213> ORGANISM: Artificial Sequence
<220> FEATURE:
<223> OTHER INFORMATION: Primer 1

<400> SEQUENCE: 12
aatgcaaatg aagttccaaa tgcca                                             25

<210> SEQ ID NO 13
<211> LENGTH: 27
<212> TYPE: DNA
<213> ORGANISM: Artificial Sequence
<220> FEATURE:
<223> OTHER INFORMATION: Primer 2

<400> SEQUENCE: 13
agttggcttc aaagttcaat gatgaga                                           27

<210> SEQ ID NO 14
<211> LENGTH: 18
<212> TYPE: DNA
```

```
<213> ORGANISM: Artificial Sequence
<220> FEATURE:
<223> OTHER INFORMATION: Probe 1

<400> SEQUENCE: 14
tatcgccttt tacatcca                                                   18

<210> SEQ ID NO 15
<211> LENGTH: 16
<212> TYPE: DNA
<213> ORGANISM: Artificial Sequence
<220> FEATURE:
<223> OTHER INFORMATION: Probe 2

<400> SEQUENCE: 15
tcgccttttg catcca                                                     16

<210> SEQ ID NO 16
<211> LENGTH: 435
<212> TYPE: DNA
<213> ORGANISM: Glycine max
<220> FEATURE:
<221> NAME/KEY: allele
<222> LOCATION: (83)..(83)
<223> OTHER INFORMATION: TGTA insertion or deletion
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (418)..(419)
<223> OTHER INFORMATION: n is a, c, g, or t

<400> SEQUENCE: 16
tcagatcttc ccgtctccgg ctgtgatgcc tttatcacga gatagaaact ctgattttat     60
tttattgttt attttttgttt tangtattta atttgtctct taccctacta gtagttgaca    120
ttttttattc ttaggaggat gagcaggtca actatattta ttgtgtgttt tcattatttc    180
aattattgag caaataatta aattaatgtc gccatttaat gtgggaaaag aaacatctat    240
attcatggat ttagtattgt tttgggcaag taattaattg gggctgagtg atacacgaag    300
gtgtggttgt ttaatggnca ttgtagtatg atgtaaaatg ggtgatgcat gttgtttaaa    360
tctaaaactt ttgtaatgtg gtcaaattgt caaactaatt taaaagggna ntctgatnna    420
ggagtgatct ggcgt                                                     435

<210> SEQ ID NO 17
<211> LENGTH: 20
<212> TYPE: DNA
<213> ORGANISM: Artificial Sequence
<220> FEATURE:
<223> OTHER INFORMATION: Primer 1

<400> SEQUENCE: 17
ccggctgtga tgcctttatc                                                 20
```

```
<210> SEQ ID NO 18
<211> LENGTH: 32
<212> TYPE: DNA
<213> ORGANISM: Artificial Sequence
<220> FEATURE:
<223> OTHER INFORMATION: Primer 2

<400> SEQUENCE: 18
tcctcctaag aataaaaaat gtcaactact ag                                    32

<210> SEQ ID NO 19
<211> LENGTH: 24
<212> TYPE: DNA
<213> ORGANISM: Artificial Sequence
<220> FEATURE:
<223> OTHER INFORMATION: Probe 1

<400> SEQUENCE: 19
ttatgtagta tttaatttgt ctct                                             24

<210> SEQ ID NO 20
<211> LENGTH: 24
<212> TYPE: DNA
<213> ORGANISM: Artificial Sequence
<220> FEATURE:
<223> OTHER INFORMATION: Probe 2

<400> SEQUENCE: 20
tttagtattt aatttgtctc ttac                                             24

<210> SEQ ID NO 21
<211> LENGTH: 501
<212> TYPE: DNA
<213> ORGANISM: Glycine max
<220> FEATURE:
<221> NAME/KEY: misc_feature
<222> LOCATION: (323)..(323)
<223> OTHER INFORMATION: n is a, c, g, or t

<400> SEQUENCE: 21
ccatgaacac aaaataaaca ccataccaaa atttcttgtt tttcttcaga aaaaaaaaa        60 aaaacaagac attagacagt aaaaacaatt tcatcttggt caaatgaacc aacttcaacc      120
atgatgaccc aattgaacac agattccgtc gcaagcaaaa cccgatgctt tatacagaac      180
aggcaaaagg gtattcgaaa aacacaaact tttttcaagg gagggagaga tggtgtacca      240
gtgaagttgt wgagtttgat gttggcttgg gctcggtcgg cgtagagttc ggctttgttg      300
ggttcgaggt gaatggcctg agnaagaagg tccacggcga gttcgaagtg gtcttcgacg      360
aaggcctctt tggcttttgc ttcgagatcg gaagccatgg gggagagaga gacagacaga      420
cagacacgga aagaggaaaa aggaaggttc tagagaggga aaacgaagga tcgtgatttg      480
gaattggaag agaagaaga a                                                501

<210> SEQ ID NO 22
<211> LENGTH: 20
<212> TYPE: DNA
<213> ORGANISM: Artificial Sequence
<220> FEATURE:
<223> OTHER INFORMATION: Primer 1

<400> SEQUENCE: 22
tcaagggagg gagagatggt                                                  20
```

<210> SEQ ID NO 23
<211> LENGTH: 21
<212> TYPE: DNA
<213> ORGANISM: Artificial Sequence
<220> FEATURE:
<223> OTHER INFORMATION: Primer 2

<400> SEQUENCE: 23
cgaacccaac aaagccgaac t                                              21

<210> SEQ ID NO 24
<211> LENGTH: 19
<212> TYPE: DNA
<213> ORGANISM: Artificial Sequence
<220> FEATURE:
<223> OTHER INFORMATION: Probe 1

<400> SEQUENCE: 24
ccagtgaagt tgtagagtt                                                 19

<210> SEQ ID NO 25
<211> LENGTH: 18
<212> TYPE: DNA
<213> ORGANISM: Artificial Sequence
<220> FEATURE:
<223> OTHER INFORMATION: Probe 2

<400> SEQUENCE: 25
taccagtgaa gttgttga                                                  18

<210> SEQ ID NO 26
<211> LENGTH: 2811
<212> TYPE: DNA
<213> ORGANISM: Glycine max
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (1125)..(1126)
<223> OTHER INFORMATION: n is a, c, g, or t
<220> FEATURE:
<221> NAME/KEY: misc_feature
<222> LOCATION: (1915)..(1915)
<223> OTHER INFORMATION: n is a, c, g, or t

<400> SEQUENCE: 26
ataataatag agatcaacga tgtttcaggc ttattataca tcaataatga taatttttaat    60 gattatacag taacaatata attttatatt attaattaat cttaatataa cttattcaat   120
atttcttcaa aatttattat actaaaatag ttaaaaatta tgaaatctta ctgtcacaat   180
tccaaattat aatatatatg gaatctttca tgtatataaa ctatatgaaa gcaaagaaa    240 ctatatatat atatatatat atatgaaagg gctgcaatat tattacctag ttaagcttca   300
gccatacacc tttgacattt tattagcaaa tactgctacc ttgacataaa tattgtctga   360
tagattgttc aagaacttga ataggcatg tctccaagaa cgcttgaata agattgagcc    420
aaacaccatc caaagcttta taacaaatcc aaatgtcata ctcatgtaaa attcacgatt   480
gaaaagtgaa aattcgtcat nttgaacttc aacatttggt ttttgtgtag gtctcccatc   540
aatacaaaat ttctcaagtg gctgtccaca aagatcaaga ttatcttcat aactcgaggc   600

```
attgaaactc tgtaactgtg tgctggctgg aattttttcca gttagatggt tatgtgacaa    660
atctaacacg ccgaggccat aaatttgtgt aagactcgga ggaattgaac cagccaactg    720
gtttcttgac aaatcaagag attcaagtga tgttagcttt ccaattttttg agggaatttt   780
ccctatcaaa ttgtttcttg ataaattcaa tgaaaccaat ccaaataaat tctctatttc    840
ctgtggaatt tctccagaaa agtgattgct tgagagatca atgcttttta caagtagtaa    900
cactttagtt ttgaatattc gttctgaacc tttccacatc aagagtgcnt tcaaatcata    960
tgtttggtta acccttgtgt aagtggtatt gacctgatat gaatgaagtt gataatctcc   1020
tgaagatgtt tttcgagtca ttgaagtaaa ttttttttatg catttaggaa ttttcccaga   1080
catgttattt attgagagat ccaagagttg aatgttactt aggtnncaaa tttgcaatgg   1140
taaacttcca tggaaattat ttcttttccaa acttaaaaat tgcaactctt gtaattcact   1200
cccaatccaa gcagggatga gccctgataa tttgtttttct gcaatatcta gcattactag   1260
atttgtgcaa ctcctcaagg agaaaggtat ctcatctgtt aagttgttgt ttctcaatag    1320
caatgcttga agatgaagaa gagatcccat ggatgtaggt attcttcctg aaaaattatt    1380
gtgactcaag tccaaataag ataatgactt gaaatggttc caacagtccg gaattttttcc   1440
agagaaacga ttatttgaaa ggtctaattg gtacaaagtt tcaactgtac catttgcaca    1500
taaaaatgaa agagaatctg agaatttatt tttggataaa tcaagaaaca ggaaacctcg    1560
aagaaatggt ggaatagggc catcaaattg atttgatcca agaattaggg aatggtaaag    1620
attctttagt ggaaaatttg gaattatacc atggagatta ttgtgtgaaa tattcattga    1680
aatggattct cgaaatgtta atttagccca aaaccacttt ggaaccatat cttctattcc    1740
agaatttgaa atgtcaatat ccccaaattg attttgtgtc tccaaccatt tgggaaatac    1800
tggacctagt ttgcaagatc gcaatcctat gtggctcaac tgaaacggtg aacccaatt     1860
tggactaaat gtcaaggcca ataaagagtt gtcagataac tccaagaagt ctaanttaga    1920
catgttagcg aaatgatagt cagtgagcac acccttttaag gaatttgatt gcaaatctag   1980
ttcctcaagt tgaggtggaa atttaatatc tttaggaatc tctccattta gcttgtttcc    2040
agaaagatat aattctctta aagatgagaa tattgagagg tcgggtagtg taccattgat    2100
ttgattcttg cctagatata atcgttccaa tgaatatcta gcacatccag acaagtgatg    2160
gattatcatt ggaaactctt cactcaagct attataagac atgtccaatg agcgcaaagc    2220
acatgcattc ccaaatgatt ttggaattcc accttccaaa atgtttgaag tgattgacaa    2280
agactccaac agaggtggca atttggtact mtctagaatt ttcccatttta attgattttc    2340
tgaaagatcc aatctttttca aggcagaaaa tattgaaagg tcaggaagcg taccgttgat    2400
ttgatttcct cttaagttca attcttgaag cgagaatctg gcacacccag acagccactg    2460
gagtatcgtt gatgacgtga agctgttcca ggtaagatca aggatggaaa gggaactaga    2520
aaaattgaat ttagagggct tcaatgaaag gataaaatga tcggaaaggc tacaatgaat    2580
taaacttagt tctctaagtt ttggtagctt ggcaatcatt gggaggaagc tatgagaagt    2640
gttgagatta gatatggagt ccaaggaaag atgggttaaa gaaatgagat tagacagcca    2700
acgatctcca tcgtcaattt tgagagcacc accataaatat gatcggcctc caagataaag    2760
cttcagcaaa tttggaaggt tcccaagtcg ggacggtaca cttcctcctc c             2811
```

<210> SEQ ID NO 27
<211> LENGTH: 24
<212> TYPE: DNA

```
<213> ORGANISM: Artificial Sequence
<220> FEATURE:
<223> OTHER INFORMATION: Primer

<400> SEQUENCE: 27
gtgattgaca aagactccaa caga                                          24

<210> SEQ ID NO 28
<211> LENGTH: 19
<212> TYPE: DNA
<213> ORGANISM: Artificial Sequence
<220> FEATURE:
<223> OTHER INFORMATION: Primer 2

<400> SEQUENCE: 28
cggtacgctt cctgacctt                                                19

<210> SEQ ID NO 29
<211> LENGTH: 18
<212> TYPE: DNA
<213> ORGANISM: Artificial Sequence
<220> FEATURE:
<223> OTHER INFORMATION: Probe

<400> SEQUENCE: 29
tggcaatttg gtactatc                                                 18

<210> SEQ ID NO 30
<211> LENGTH: 19
<212> TYPE: DNA
<213> ORGANISM: Artificial Sequence
<220> FEATURE:
<223> OTHER INFORMATION: Probe 2

<400> SEQUENCE: 30
caatttggta ctctctaga                                                19
```